United States Patent
Sporn

(10) Patent No.: US 12,370,202 B2
(45) Date of Patent: Jul. 29, 2025

(54) METHODS AND COMPOSITIONS FOR INHIBITING THE NLRP3 INFLAMMASOME AND/OR LON PROTEASE

(71) Applicant: TRITERPENOID THERAPEUTICS, INC., Lebanon, NH (US)

(72) Inventor: Michael B. Sporn, Tunbridge, VT (US)

(73) Assignee: TRITERPENOID THERAPEUTICS, INC., Braintree, MA (US)

( * ) Notice: Subject to any disclaimer, the term of this patent is extended or adjusted under 35 U.S.C. 154(b) by 828 days.

(21) Appl. No.: 17/430,065

(22) PCT Filed: Feb. 12, 2020

(86) PCT No.: PCT/US2020/017956
§ 371 (c)(1),
(2) Date: Aug. 11, 2021

(87) PCT Pub. No.: WO2020/167969
PCT Pub. Date: Aug. 20, 2020

(65) Prior Publication Data
US 2022/0133748 A1 May 5, 2022

Related U.S. Application Data

(60) Provisional application No. 62/806,256, filed on Feb. 15, 2019, provisional application No. 62/913,966, filed on Oct. 11, 2019, provisional application No. 62/947,928, filed on Dec. 13, 2019.

(51) Int. Cl.
*A61K 31/58* (2006.01)
*A61K 33/243* (2019.01)
*A61P 35/00* (2006.01)

(52) U.S. Cl.
CPC .......... *A61K 31/58* (2013.01); *A61K 33/243* (2019.01); *A61P 35/00* (2018.01)

(58) Field of Classification Search
CPC ........ A61K 31/58; A61K 33/243; A61P 35/00
See application file for complete search history.

(56) References Cited

U.S. PATENT DOCUMENTS

| | | | |
|---|---|---|---|
| 7,435,755 B2 | 10/2008 | Konopleva et al. | |
| 2006/0052390 A1 | 3/2006 | Schreiner et al. | |
| 2009/0018146 A1 | 1/2009 | Gutterman et al. | |
| 2013/0324599 A1 | 12/2013 | Anderson et al. | |
| 2014/0255432 A1 | 9/2014 | Baiocchi et al. | |
| 2017/0267713 A1* | 9/2017 | Gribble ................ | C07D 233/54 |
| 2018/0127379 A1 | 5/2018 | Sporn et al. | |
| 2019/0029987 A1* | 1/2019 | Beer .................... | A61K 31/225 |
| 2022/0160879 A1 | 5/2022 | Sporn et al. | |

FOREIGN PATENT DOCUMENTS

| | | |
|---|---|---|
| WO | WO1993005789 | 4/1993 |
| WO | 2002047611 A2 | 6/2002 |
| WO | WO2005123127 | 12/2005 |
| WO | WO2008124660 | 10/2008 |
| WO | 2009023845 A2 | 2/2009 |
| WO | 2018200608 A1 | 11/2018 |
| WO | 2019025467 A1 | 2/2019 |
| WO | 2020210573 A1 | 10/2020 |

OTHER PUBLICATIONS

Cao , Pharmacological Research, 100, 2015, 135-147 (Year: 2015).*
Merriam-Webster (Merriam-Webster, Abrogate, url= https://www.merriam-webster.com/dictionary/abrogate#:~:text=formal%20%3A%20to%20suppress%20or%20prevent,heart%20transplant%20have%20been%20encouraging, accessed Dec. 10, 2024 (Year: 2024).*
Cao, et al., Pharmacological Research, 100:135-147 (2015).
Chauhan, et al., Blood, 103(8):3158-3166 (2004).
Hu et al., Blood, 136(S1):4 (2020).
Ortiz, F. et al., "Melatonin blunts the mitochondrial/NLRP3 connection and protects against radiation-induced oral mucositis," J. Pineal Res., 2014, vol. 58(1), 17 pages.
International Search Report and Written Opinion issued on May 11, 2020 for International Patent Application No. PCT/US2020/017956, 32 pages.
Anjum et al., Biomedicine & Pharmacotherapy, 92, 681-689, 2017.
Bernstein, et al., "The mitochondrial ATP-dependent LON protease: a novel target in lymphoma death mediated by the synthetic triterpenoid CDDO and its derivatives," Blood, Journal of The American Society of Hematology, 2012, 18 pp.
Cleasby, et al., "Structure of the BTB Domain of Keap1 and Its Interaction with the Triterpenoid Antagonist CDDO," PLOS One, vol. 9, Issue 6, Jun. 2014, 10 pp.
Kamble, et al., "In-Silico Evidence for Binding of Pentacyclic Triterpenoids to Keap1-Nrf2 Protein-Protein Binding Site," Combinatorial Chemistry & High Throughput Screening, 2017, 20 pp.
Minchenko, et al., "Glucose Deprivation Affects the Expression of LONP1 and Cathepsins in IRE1 Knockdown U87 Glioma Cells," Experimental Articles, vol. 9, No. 6, 2016, 12 pp.
Pinti, et al., "Mitochondrial Lon protease at the crossroads of oxidative stress, ageing and cancer," Cellular and Molecular Life Sciences, 2015, 18 pp.

* cited by examiner

*Primary Examiner* — Susanna Moore
*Assistant Examiner* — LuisAlberto Gonzalez
(74) *Attorney, Agent, or Firm* — Neal, Gerber & Eisenberg LLP

(57) ABSTRACT

The present invention relates to methods, compositions, and combinations for inhibiting the NLRP3 inflammasome and/or LON protease as well as methods, compositions, and combinations for treating cancer, particularly blood cancer or brain cancer. In certain aspects, the compositions and combinations include a synthetic triterpenoid, such as 1-[2-Cyano-3,12-dioxooleana-1,9(11)-dien-28-oyl]-4(-pyridin-2-yl)-1H-imidazole ("CDDO-2P-Im") and 1-[2-Cyano-3,12-dioxooleana-1,9(11)-dien-28-oyl]-4(-pyridin-3-yl)-1H-imidazole ("CDDO-3P-Im").

19 Claims, 22 Drawing Sheets

(Contiunued)

METHODS AND COMPOSITIONS FOR INHIBITING THE NLRP3 INFLAMMASOME AND/OR LON PROTEASE

CROSS REFERENCE TO RELATED APPLICATIONS

This application is a national stage entry pursuant to 35 U.S.C. § 371 of International Application No. PCT/US2020/017956, which was filed on Feb. 12, 2020, which claims priority to U.S. Patent Application No. 62/806,256, which was filed on Feb. 15, 2019; U.S. Patent Application No. 62/913,966, which was filed on Oct. 11, 2019 and U.S. Patent Application No. 62/947,928, which was filed on Dec. 13, 2019, the entire contents of which are incorporated herein by reference.

TECHNICAL FIELD

The present invention relates to methods and compositions for inhibiting the NLRP3 inflammasome and/or LON protease.

BACKGROUND

Therapy-resistance is a major challenge in the treatment of cancers, including childhood brain tumors and blood cancers such as multiple myeloma.

Multiple myeloma (MM) is a blood cancer that results from the malignant proliferation of bone marrow plasma cells. MM remains a fatal disease despite all available therapies, with a 5-year survival rate of only 50%. The Surveillance, Epidemiology, and End Results (SEER) Program estimates that in 2018 in the United States, there will be 30,280 new cases and 12,590 deaths from MM, with over 150,000 adults actively living with MN.

Gliomas (Grade I-IV) are lethal primary brain tumors that make up eighty percent of all malignant brain tumors and about thirty percent of all central nervous system tumors. Low-grade gliomas (grade I & II) increase in time to become high grade gliomas (Grade III & IV). These recur in more than 90% of cases and have a median survival rate of 14 months and a 5-year survival rate of less than 10%. Glioblastoma multiforme (GBM) is the most common primary brain tumor. Survival rates in GBM are poor with less than 5% of patients surviving 5 years following diagnosis, with no notable improvement in population statistics in the last three decades, highlighting a desperate need for new and innovative approaches to treat this lethal disease.

For multiple myeloma, most patients will be treated with a three-drug regimen that includes: a proteasome inhibitor (PI) such as bortezomib (brand name: Velcade), carfilzomib (brand name: Kyprolis) or ixazomib (brand name: Ninlaro); an immunomodulatory drug such as lenalidomide (brand name: Revlimid); and a corticosteroid such as dexamethasone (Dex). However, prolonged exposure to these agents is invariably associated with the development of drug resistance.

For adult patients with newly diagnosed GBM, temozolomide (TMZ) is now given concomitantly with radiation therapy and then as maintenance treatment. Despite the addition of TMZ to the standard of care over a decade ago, the average length of survival for a patient with GBM remains at 14 months. Moreover, prolonged exposure to TMZ is associated with significant toxicity, including profound lymphopenia, and with the development of drug resistance. Because GBM is currently often incurable, there is a dire need for novel drugs that target mechanisms that underlie therapy resistance in GBM and that can enhance the response TMZ and radiation.

Multiple mechanisms of drug resistance have been defined, including activation of the inflammasome. In addition, recent evidence suggests an important role of the mitochondrial protein LON protease (LONP1) and other mitochondrial proteases having homology to LONP1 (e.g., Clp protease).

Inflammasomes are multi-protein complexes consisting of nucleotide-binding and oligomerization domain (NOD)-like receptor (NLR), the adaptor protein (ASC: apoptosis-associated speck-like protein containing CARD), and pro-caspase-1. Among NLRs, NLRP1, NLRP2, NLRP3, NLRP4, NLRP6, NLRP12, and NLRP14 are known to form multi-protein complexes and are grouped into a canonical inflammasome pathway. Among NLRs, NLRP3 has emerged as a key mediator of therapy resistance as it senses the widest array of stimuli, is activated by both radiation therapy and chemotherapy. The NLRP3 inflammasome is also activated by adenosine triphosphate in LPS-activated macrophages, leading to caspase-1 activation and IL-1β secretion.

$LONP_1$ is upregulated under oxidative and hypoxic stress, and is a critical mediator of stress adaptation by tumor cells that is induced in GBM cells following exposure to either TMZ or radiation. Moreover, inhibition of LONP1 promotes cancer cell death and enhances sensitivity of tumor cells to anticancer drugs. Mechanisms mediating effects of LONP1 include modulation of mitophagy via regulation of the PINK1/Parkin complex, and suppression of the activation of the NLRP3 inflammasome, regulated by Parkin at the mitochondrial membrane.

There is a dire need for novel drugs that target mechanisms that underlie the development of therapy resistance in cancers generally, and multiple myeloma and childhood and adult brain tumors particularly, that can enhance the response rates to currently active agents.

SUMMARY OF THE INVENTION

In one aspect, this disclosure provides a method for inhibiting an inflammasome comprising administering a synthetic triterpenoid to a patient in need thereof. In some embodiments, the inflammasome is an NLRP3 inflammasome. In some embodiments, the patient is undergoing a concomitant cancer therapy susceptible to resistance, such as treatment with a proteasome inhibitor (PI), treatment with a steroid, treatment with a vaccine and/or immunotherapy, or radiation therapy. In some embodiments, the patient is a cancer patient (e.g., a pediatric patient having a brain tumor or a patient having multiple myeloma).

In one aspect, this disclosure provides a method for inhibiting a mitochondrial protease, preferably LON protease (LONP1), comprising administering a synthetic triterpenoid to a patient in need thereof. In some embodiments, the patient is undergoing a concomitant cancer therapy susceptible to resistance, such as treatment with an alkylating agent, such as temozolomide (TMZ), and/or radiation therapy. In some embodiments, the patient is a cancer patient (e.g., an adult or pediatric patient having a brain tumor, such as glioblastoma).

In one aspect, this disclosure provides a method for treating a blood cancer (e.g., multiple myeloma) comprising administering a synthetic triterpenoid to a patient in need thereof. In some embodiments, the patient is a pediatric cancer patient. In other such embodiments, the patient is an adult cancer patient. In some embodiment, the method further comprises co-administering a proteasome inhibitor to the patient. In some such embodiments, the proteasome inhibitor and the synthetic triterpenoid are administered substantially simultaneously. In some embodiments, the method further comprises treating the patient with radiation therapy.

In one aspect, this disclosure provides a method for treating brain cancer (e.g., glioblastoma) comprising administering a synthetic triterpenoid to a patient in need thereof. In some embodiments, the patient is a pediatric cancer patient (e.g., a pediatric patient having a brain tumor). In other such embodiments, the patient is an adult cancer patient. In some embodiment, the method further comprises co-administering an alkylating agent to the patient. In some embodiments, the alkylating agent and the synthetic triterpenoid are administered substantially simultaneously. In some such embodiments, the alkylating agent is TMZ. In some embodiments, the method further comprises treating the patient with radiation therapy.

In one aspect, this disclosure provides a method for treating a solid tumor comprising administering a synthetic triterpenoid to a patient in need thereof. In some embodiments, the patient is an ovarian cancer patient. In some embodiments, the method further comprises co-administering a platinum compound to the patient. In some embodiments, the platinum compound and the synthetic triterpenoid are administered substantially simultaneously. In some such embodiments, the platinum compound is cisplatin.

In one aspect, this disclosure provides a method for preventing or reducing resistance to a therapy comprising administering a synthetic triterpenoid to a patient in need thereof. In some embodiments, the therapy is treatment with a proteasome inhibitor (PI), treatment with a steroid, treatment with a vaccine and/or immunotherapy, or radiation therapy. In some embodiments, the therapy is treatment with an oral chemotherapy agent, such as temozolomide (TMZ) or another alkylating agent, and/or radiation therapy. In some embodiments, the therapy is treatment with a platinum compound, such as cisplatin, or another injectable chemotherapy agent. In some embodiments, the patient is a cancer patient (e.g., an adult or pediatric patient having a brain tumor or a patient having a blood cancer such as multiple myeloma or a patient having ovarian cancer).

In one aspect, this disclosure provides a method for enhancing cancer cell death, the method comprising co-administering a proteasome inhibitor and a synthetic triterpenoid to a patient in need thereof, wherein the synthetic triterpenoid reduces resistance of the cancer cells to the proteasome inhibitor and/or improves anticancer effect of the proteasome inhibitor. In some embodiments, the proteasome inhibitor and the synthetic triterpenoid are administered substantially simultaneously. In some embodiments, the cancer cells comprise proteasome inhibitor-resistant multiple myeloma cells. In some embodiments, the patient has a blood cancer. In some such embodiments, the patient has a blood cancer selected from the group consisting of multiple myeloma, diffuse large B cell lymphoma, and mantle-cell lymphoma. In some embodiments, the patient has a solid tumor.

In one aspect, this disclosure provides a method for enhancing cancer cell death, the method comprising co-administering an oral chemotherapeutic agent (e.g., TMZ or another alkylating agent) and a synthetic triterpenoid to a patient in need thereof, wherein the synthetic triterpenoid reduces resistance of the cancer cells to the oral chemotherapeutic agent and/or improves anticancer effect of the oral chemotherapeutic agent. In some embodiments, the oral chemotherapeutic agent and the synthetic triterpenoid are administered substantially simultaneously. In some embodiments, the cancer cells comprise TMZ-resistant brain tumor cells. In some embodiments, the patient has a brain cancer. In some such embodiments, the patient has GBM.

In one aspect, this disclosure provides a method for enhancing cancer cell death, the method comprising co-administering a platinum compound (e.g., cisplatin) and a synthetic triterpenoid to a patient in need thereof, wherein the synthetic triterpenoid reduces resistance of the cancer cells to the platinum compound and/or improves anticancer effect of the platinum compound. In some embodiments, the platinum compound and the synthetic triterpenoid are administered substantially simultaneously. In some embodiments, the cancer cells comprise cisplatin-resistant ovarian cancer cells. In some such embodiments, the patient has ovarian cancer.

In some embodiments of any aspects disclosed herein, the synthetic triterpenoid is an analog or derivative of 1-[2-Cyano-3,12-dioxooleana-1,9(11-dien-28-oyl) (CDDO-Im) or a pharmaceutically acceptable salt thereof and, in particular, a pyridyl analog such as CDDO-2P-Im or CDDO-3P-Im. In some such embodiments, the synthetic triterpenoid is 1-[2-Cyano-3,12-dioxooleana-1,9(11)-dien-28-oyl]-4(-pyridin-2-yl)-1H-imidazole (CDDO-2P-Im) or a pharmaceutically acceptable salt thereof. In some embodiments of any aspects disclosed herein, the synthetic triterpenoid is administered orally.

DETAILED DESCRIPTION

Figure 1:
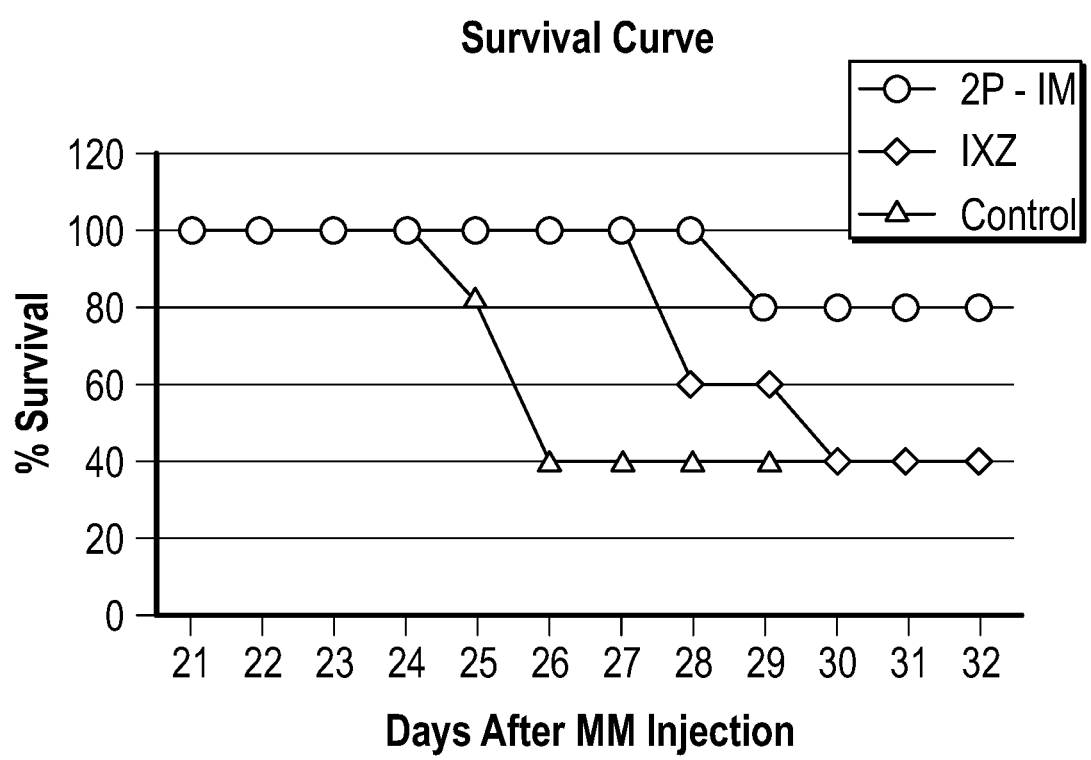
FIG. 1 is a survival curve. Survival of mice receiving either ixazomib (IXZ) or CDDO-2P-Im starting 21 days after tumor cell injection (n=5 mice per group). CDDO-2P-Im is active in the 5T3MM preclinical model of multiple myeloma.

This detailed description is intended only to acquaint others skilled in the art with the present invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

A. DEFINITIONS

As used in the specification and the appended claims, unless specified to the contrary, the following terms have the meaning indicated:

The term "about" as used herein, means approximately, and in most cases within 10% of the stated value.

The term "brain tumor" includes a glioma, such as an astrocytoma (e.g., anaplastic astrocytoma), glioblastoma, ependymoma (e.g., anaplastic ependymoma or myxopapillary ependymoma), oligodendroglioma (e.g., anaplastic oligodendroglioma or anaplastic oligoastrocytoma), and all gliomas classified under WHO Grade 1 to Grade 4.

The term "pharmaceutically acceptable" is used adjectivally to mean that the modified noun is appropriate for use as a pharmaceutical product for human use or as a part of a pharmaceutical product for human use.

The terms "treat", "treating" and "treatment" refer to a method of alleviating or abrogating a condition, disorder, or disease and/or the attendant symptoms thereof.

B. METHODS OF TREATMENT

In one aspect, this disclosure provides a method for inhibiting an inflammasome, preferably NLRP3 inflammasome. The method comprises administering a synthetic triterpenoid to a patient in need thereof. In some embodiments, the synthetic triterpenoid is 1-[2-Cyano-3,12-dioxooleana-1,9(11)-dien-28-oyl]-4(-pyridin-2-yl)-1H-imidazole. In some embodiments, the synthetic triterpenoid is administered orally.

In one aspect, this disclosure provides a method for treating a disease or condition that is at least partially mediated by inflammasome activity, particularly NLRP3 inflammasome activity. The method comprises administering a synthetic triterpenoid to a patient in need thereof.

In some embodiments, the synthetic triterpenoid is 1-[2-Cyano-3,12-dioxooleana-1,9(11)-dien-28-oyl]-4(-pyridin-2-yl)-1H-imidazole. In some embodiments, the synthetic triterpenoid is administered in a therapeutically effective amount to inhibit inflammasome activity, and preferably NLRP3 inflammasome activity.

In some embodiments, the disease or condition is selected from the group consisting of cancer, cancer therapy resistance, autoimmune diseases, inflammatory diseases (e.g., Crohn's disease and other diseases associated with aberrant inflammatory responses, including neuropsychiatric disorders and, particularly, depression), neurodegenerative diseases (e.g., Alzheimer's disease (AD), Parkinson's disease (PD), amyotrophic lateral sclerosis (ALS), multiple sclerosis (MS), Huntington disease), diseases of the eye (e.g., diabetic retinopathy, macular degeneration), diseases of the lung (e.g., Chronic Obstructive Pulmonary Disease (COPD), emphysema, pulmonary fibrosis, bronchopulmonary dysplasia), diseases of the liver (e.g., chronic metabolic disease, liver injury from various toxins, atherosclerosis, chronic kidney disease (CKD), including CKD resulting from diabetes, acute renal injury, and aging. In some such embodiments, the cancer is a blood cancer, such as leukemia, lymphoma, or myeloma; in particular embodiments the blood cancer is, for example, Hodgkin or non-Hodgkin lymphoma (e.g., diffuse large B cell lymphoma or mantle cell lymphoma). In other such embodiments, the cancer involves a solid tumor, such as breast cancer, ovarian cancer, or brain cancer (e.g., medulloblastoma or glioblastoma). In some such embodiments, the cancer therapy resistance is resistance to proteasome inhibitor (PI) therapy. In some such embodiments, the cancer therapy resistance is resistance to an oral chemotherapeutic agent, such as an alkylating agent (e.g., TMZ). In some such embodiments, the cancer therapy resistance is resistance to radiation therapy.

In some embodiments, the patient is an adult patient. In some embodiments, the patient is a pediatric patient. In some such embodiments, the pediatric patient has a brain tumor, such as glioblastoma or medulloblastoma.

In some embodiments, the patient is a cancer patient. In some such embodiments, the cancer patient is suffering from cancer-related pain mediated by an inflammasome. In some such embodiments, the cancer-related pain is related to proteasome inhibitor (PI) therapy. In some such embodiments, the cancer patient is suffering from lymphopenia related to treatment with an oral chemotherapeutic agent.

In one aspect, this disclosure provides a method for treating cancer-related pain. The method comprises administering a synthetic triterpenoid to a patient in need thereof. In some embodiments, the cancer-related pain is neuropathy. In some embodiments, the cancer-related pain is related to proteasome inhibitor (PI) therapy. In some embodiments, the cancer-related pain is mediated by an inflammasome, particularly NLRP3 inflammasome. In some embodiments, the synthetic triterpenoid is 1-[2-Cyano-3,12-dioxooleana-1,9(11)-dien-28-oyl]-4(-pyridin-2-yl)-1H-imidazole.

In one aspect, this disclosure provides a method for treating cancer, particularly a blood cancer. In certain embodiments, the method comprises co-administering a proteasome inhibitor and a synthetic triterpenoid to a patient in need thereof. In some embodiments, the proteasome inhibitor is bortezomib, carfilzomib, MLN9708, or ixazomib. In some embodiments, the synthetic triterpenoid is 1-[2-Cyano-3,12-dioxooleana-1,9(11)-dien-28-oyl]-4(-pyridin-2-yl)-1H-imidazole. In some embodiments, the PI and the synthetic triterpenoid are co-administered to the patient in a substantially simultaneous manner (e.g., within about 5 min of each other), in a sequential manner, or both. It is contemplated, for example, that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient. In some embodiments, the PI and the synthetic triterpenoid are administered in separate pharmaceutical compositions. In some embodiments, the PI and the synthetic triterpenoid are administered in the same pharmaceutical composition. In some embodiments, the PI and the synthetic triterpenoid act additively to treat the cancer. In some embodiments, the PI and the synthetic triterpenoid act synergistically to treat the cancer.

In one aspect, this disclosure provides a method for treating cancer, particularly a solid tumor. In certain embodiments, the method comprises co-administering a chemotherapeutic agent and a synthetic triterpenoid to a patient in need thereof. In some embodiments, the chemotherapeutic agent is an injectable (e.g., intravenous) chemotherapeutic agent, such as a platinum compound. In some such embodiments, the platinum compound is cisplatin or oxaliplatin. In some embodiments, the synthetic triterpenoid is 1-[2-Cyano-3,12-dioxooleana-1,9(11)-dien-28-oyl]-4(-pyridin-2-yl)-1H-imidazole. In some embodiments, the injectable chemotherapeutic agent and the synthetic triterpenoid are co-administered to the patient in a substantially simultaneous manner (e.g., within about 5 min of each other), in a sequential manner, or both. It is contemplated, for example, that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient. In some embodiments, the injectable chemotherapeutic agent and the synthetic triterpenoid are administered in separate pharmaceutical compositions. In some embodiments, the injectable chemotherapeutic agent and the synthetic triterpenoid are administered in the same pharmaceutical composition. In some embodiments, the injectable chemotherapeutic agent and the synthetic triterpenoid act additively to treat the cancer. In some embodiments, the injectable chemotherapeutic agent and the synthetic triterpenoid act synergistically to treat the cancer.

In one aspect, this disclosure provides a method for treating cancer, particularly a solid tumor. In certain embodiments, the method comprises co-administering an oral chemotherapeutic agent and a synthetic triterpenoid to a patient in need thereof. In some embodiments, the oral chemotherapeutic agent is an alkylating agent. In some such embodiments, the alkylating agent is TMZ. In some embodiments, the synthetic triterpenoid is 1-[2-Cyano-3,12-dioxooleana-1,9(11)-dien-28-oyl]-4(-pyridin-2-yl)-1H-imidazole. In some embodiments, the oral chemotherapeutic agent and the synthetic triterpenoid are co-administered to the patient in a substantially simultaneous manner (e.g., within about 5 min of each other), in a sequential manner, or both. It is contemplated, for example, that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient. In some embodiments, the oral chemotherapeutic agent and the synthetic triterpenoid are administered in separate pharmaceutical compositions. In some embodiments, the oral chemotherapeutic agent and the synthetic triterpenoid are administered in the same pharmaceutical composition. In some embodiments, the oral chemotherapeutic agent and the synthetic triterpenoid act additively to treat the cancer. In some embodiments, the oral chemotherapeutic agent and the synthetic triterpenoid act synergistically to treat the cancer.

In one aspect, this disclosure provides a method for treating multiple myeloma. The method comprises administering a synthetic triterpenoid to a patient in need thereof. In some embodiments, the synthetic triterpenoid is 1-[2-Cyano-3,12-dioxooleana-1,9(11)-dien-28-oyl]-4(-pyridin-2-yl)-1H-imidazole. In some embodiments, the method further comprises co-administering a proteasome inhibitor to the patient. In some embodiments, the method further comprises treating the patient with radiation therapy.

In one aspect, this disclosure provides a method for treating an adult or pediatric brain tumor. The method comprises administering a synthetic triterpenoid to a patient in need thereof. In some embodiments, the synthetic triterpenoid is 1-[2-Cyano-3,12-dioxooleana-1,9(11)-dien-28-oyl]-4(-pyridin-2-yl)-1H-imidazole. In some embodiments, the brain tumor is glioblastoma multiforme. In some embodiments, the method further comprises co-administering an oral chemotherapeutic agent to the patient. In some such embodiments, the oral chemotherapeutic agent is an alkylating agent, such as TMZ. In some embodiments, the method further comprises treating the patient with radiation therapy.

C. COMPOUNDS, COMPOSITIONS, AND COMBINATIONS

CDDO-Im is a synthetic triterpenoid. U.S. Pat. No. 6,974,801 and WO 2004/064723, each of which are incorporated herein by reference in their entirety, describe 1-(2-cyano-3,12-dioxooleana-1,9(11)-dien-28-oyl) imidazole (CDDO-Im), which has the chemical structure:

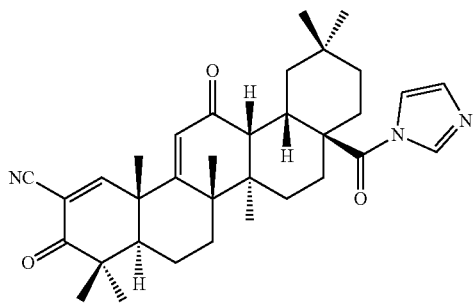

U.S. Pat. No. 9,896,475, which is incorporated herein by reference in its entirety, describes analogs and derivatives of CDDO-Im, including pyridyl analogs of CDDO-Im, which are more stable in human plasma and achieve a higher concentration in target tissues such as liver, pancreas, kidney and lungs.

Particular synthetic triterpenoids described herein include compounds having the structure of Formula I and pharmaceutically acceptable salts thereof:

Formula I

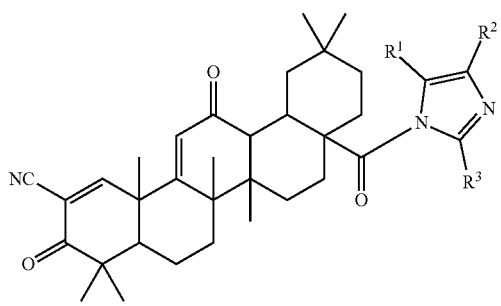

wherein one or more of $R^1$, $R^2$ or $R^3$ is independently a heteroaryl group (preferably a pyridyl group), cycloalkyl group, heterocyclyl group, carboxamide group, nitrile group, haloalkyl group, or acyl group, each of which may be substituted or unsubstituted where appropriate, and the remaining R groups are hydrogen. In a particular embodiment, $R^2$ is a substituted or unsubstituted aryl group, heteroaryl group, cycloalkyl group or heterocyclyl group, and $R^1$ and $R^3$ are hydrogen.

The term "heteroaryl" refers to a five- or six-membered aromatic ring structure, wherein at least one of the aromatic ring atoms is nitrogen, oxygen or sulfur, and wherein the monovalent group is composed of carbon, hydrogen, aromatic nitrogen, aromatic oxygen or aromatic sulfur. Non-limiting examples of aryl groups include acridinyl, furanyl, imidazoimidazolyl, imidazopyrazolyl, imidazopyridinyl, imidazopyrimidinyl, indolyl, indazolinyl, methylpyridyl, oxazolyl, phenylimidazolyl, pyridyl, pyrrolyl, pyrimidyl, pyrazinyl, quinolyl, quinazolyl, quinoxalinyl, tetrahydroquinolinyl, thienyl, triazinyl, pyrrolopyridinyl, pyrrolopyrimidinyl, pyrrolopyrazinyl, pyrrolotriazinyl, pyrroloimidazolyl, and chromenyl, wherein the point of attachment is one of the aromatic atoms. In particular embodiments, the heteroaryl is a pyridyl group. In some such embodiments, the pyridyl group is unsubstituted. In other such embodiments, the pyridyl group is substituted.

"Cycloalkyl" means a non-aromatic mono- or multicyclic ring system including about 3 to about 10 carbon atoms, preferably about 5 to about 10 carbon atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Heterocyclyl" or "heterocycloalkyl" means a non-aromatic saturated monocyclic or multicyclic ring system including about 3 to about 10 ring atoms, preferably about 5 to about 10 ring atoms, in which one or more of the atoms in the ring system is an element other than carbon, for example nitrogen, oxygen or sulfur, alone or in combination. Preferred heterocyclyls contain about 5 to about 6 ring atoms. The prefix aza, oxa or thia before the heterocyclyl root name means that at least a nitrogen, oxygen or sulfur atom respectively is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. Non-limiting examples of suitable bicyclic heterocyclyl rings include decahydro-isoquinoline, decahydro-[2,6]naphthyridine, and the like.

As used herein, a "carboxamide" or "carboxamide group" refers to a —C(=O)NH$_2$ group.

The term "nitrile" or "nitrile group" is intended to refer to a —C≡N group.

As used herein, "alkyl" or "alkyl group" includes linear or branched saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include, but are not limited to, methyl, ethyl, n-propyl, isopropyl, n-butyl, isobutyl, sec-butyl, t-butyl, n-pentyl, sec-pentyl, 3-(2-methyl)butyl, 2-pentyl, 2-methylbutyl, n-hexyl, and 2-methylpentyl. In particular embodiments, an alkyl of this invention is a $C_{1-6}$ alkyl, $C_{1-5}$ alkyl, $C_{1-4}$ alkyl, $C_1$-3 alkyl, or $C_{1-2}$ alkyl.

The term "haloalkyl group" refers to a linear or branched alkyl group substituted by one or more halogen atoms, the same or different, optionally selected from fluorine, chlorine, bromine, and iodine. Examples of this group include fluoromethyl, difluoromethyl, trifluoromethyl, trichloromethyl, 2,2,2-trifluoroethyl, 2,2,2-trichloroethyl, 2,2,3,3-tetrafluoropropyl, 2,2,3,3,3-pentafluoropropyl.

"Acyl," as used herein alone or as part of another group, refers to a —C(=O)R radical, where R is, e.g., an aryl, alkyl, alkenyl, alkynyl, cycloalkyl, or haloalkyl group. When the R group contains a halogen, the group is termed a "haloacyl" group. An example is a trifluoroacetyl group.

The term "aryl" refers to a monovalent group with an aromatic carbon atom as the point of attachment, said carbon atom forming part of a five- or six-membered aromatic ring structure wherein the ring atoms are all carbon, and wherein the monovalent group is composed of carbon and hydrogen. Non-limiting examples of aryl groups include phenyl, methylphenyl, (dimethyl)phenyl, -ethylphenyl, propylphenyl, —C$_6$H$_4$CH(CH$_3$)$_2$, —C$_6$H$_4$CH(CH$_2$)$_2$, methylethylphenyl, vinylphenyl, naphthyl, and the monovalent group derived from biphenyl. In particular embodiments, the aryl is a phenyl group.

As used herein, "alkenyl" or "alkenyl group" refers to an unsaturated branched, straight-chain or cyclic monovalent hydrocarbon radical having at least one carbon-carbon double bond derived by the removal of one hydrogen atom from a single carbon atom of a parent alkene. The radical may be in either the cis or trans conformation about the double bond(s). Examples of alkenyl include, but are not limited to, ethenyl, propenyls, such as prop-1-en-1-yl, prop-1-en-2-yl, prop-2-en-1-yl, prop-2en-2-yl, cycloprop-1-en-1-yl; cycloprop-2-en-1-yl; butenyls such as but-1-en-1-yl, but-1-en-2-yl, 2-methyl-prop-1-en-1yl, but-2-en-1-yl, but-2-en-1-yl, but-2-en-2-yl, buta-1,3-dien1-yl, beta-1,3-dien-2-yl, cyclobut-1-en-1-yl, cyclobut-1-en3-yl, cyclobuta-1,3-dien-1-yl.

As used herein, an "alkynyl" or "alkynyl group" refers to an unsaturated branched, straight-chain or cyclic monovalent hydrocarbon radical having at least one carbon-carbon triple bond derived by the removal of one hydrogen atom from a single carbon atom of a parent alkyne. Examples of alkynyl groups include, but are not limited to, ethynyl, propynyl, butynyls, propargyl, and the like.

Any of the groups described herein may be unsubstituted or optionally substituted. When modifying a particular group, "substituted" means that the group the term modifies may, but does not have to, be substituted. Substitutions include the replacement of an available hydrogen with an alkyl, alkenyl, alkynyl, aryl, haloalkyl, haloacyl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, alkoxyalkoxy, acyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, or heterocyclyl.

Any undefined valency on an atom of a structure shown in this application implicitly represents a hydrogen atom bonded to the atom.

In some embodiments of any aspects disclosed herein, a synthetic triterpenoid has the structure of Formula II and pharmaceutically acceptable salts thereof:

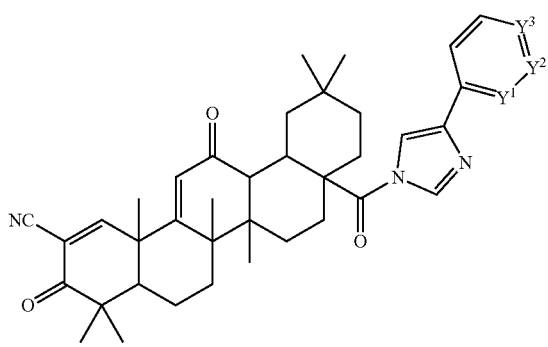

Formula II wherein one of $Y^1$, $Y^2$, or $Y^3$, is N and the remaining Y groups are each CH. In a particular embodiment, $Y^1$ is N and $Y^2$ and $Y^3$ are CH. In another particular embodiment, $Y^2$ is N and $Y^1$ and $Y^3$ are CH. In another particular embodiment, $Y^3$ is N and $Y^1$ and $Y^2$ are CH.

A particularly preferred synthetic triterpenoid is 1-[2-Cyano-3,12-dioxooleana-1,9(11)-dien-28-oyl]-4(-pyridin-2-yl)-1H-imidazole (CDDO-2P-Im), which is depicted structurally as:

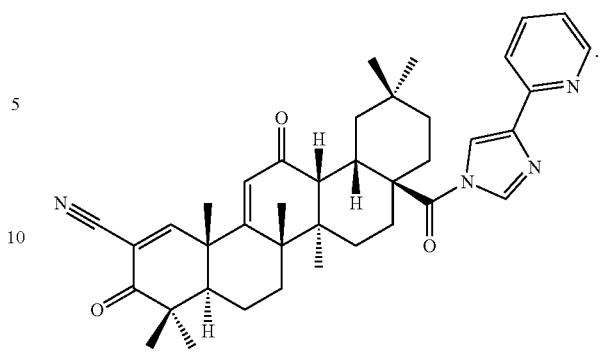

Another particularly preferred synthetic triterpenoid is 1-[2-Cyano-3,12-dioxooleana-1,9(11)-dien-28-oyl]-4(-pyridin-3-yl)-1H-imidazole (CDDO-3P-Im), which is depicted structurally as:

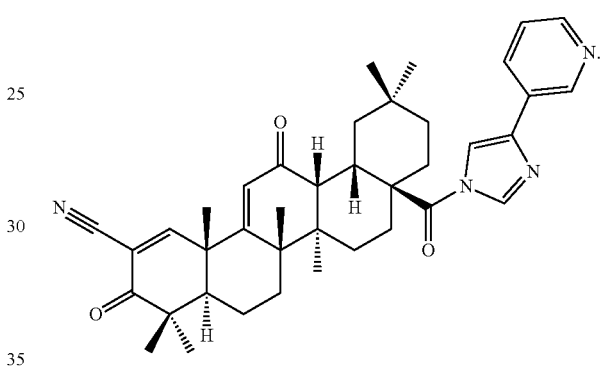

In some embodiments of any aspects disclosed herein, a synthetic triterpenoid may be present in a pharmaceutical composition in the form of acid or base addition salts. Acid addition salts may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Suitable base addition salts include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" is intended to encompass any and all acceptable salt forms.

Pharmaceutical compositions disclosed herein comprise a synthetic triterpenoid, preferably CDDO-2P-Im or a pharmaceutically acceptable salt thereof. In some embodiments, the pharmaceutical composition is an oral dosage form, preferably a solid oral dosage form (e.g., a tablet). In some such embodiments, the solid oral dosage form may comprise pharmaceutically acceptable excipients such as excipients that function as binders, glidants, lubricants, and fillers. Thus, a solid oral dosage form comprising a synthetic triterpenoid, further optionally comprises one or more conventional pharmaceutically acceptable excipients.

A synthetic triterpenoid, preferably CDDO-2P-Im or a pharmaceutically acceptable salt thereof, may be administered in a single or divided dose to provide a total daily dose. The total daily dose of a synthetic triterpenoid (administered in single or divided doses) may typically be from about 0.1 to about 5000 mg, or from about 1 to about 500 mg, or from about 1 to about 100 mg, or from about 5 to about 50 mg.

Factors affecting the preferred dosage amount and frequency include the type, age, weight, sex, diet, and condition of the patient; the severity of the pathological condition; pharmacological considerations, such as the activity, efficacy, pharmacokinetic, and toxicology profiles of the particular compound or salt used; whether a drug delivery system is utilized; and the specific drug combination, if any. Thus, the dosage regimen actually employed can vary widely, and therefore, can derive from those set forth herein.

1. Use in Blood Cancer Treatment

In one aspect, this disclosure provides a synthetic triterpenoid, such as CDDO-2P-Im, CDDO-3P-Im, or a pharmaceutically acceptable salt thereof, for use as a single agent or in combination with one or more additional therapeutic agents (e.g., a proteasome inhibitor) in a method of treating blood cancer, such as multiple myeloma. In such aspects, a synthetic triterpenoid is administered to a patient to treat a blood cancer, such as multiple myeloma. In some embodiments, the synthetic triterpenoid is CDDO-2P-Im or a pharmaceutically acceptable salt thereof. In some embodiments, CDDO-2P-Im or a pharmaceutically acceptable salt thereof is co-administered with one or more therapeutic agents to treat a blood cancer, such as multiple myeloma.

In some embodiments, a synthetic triterpenoid is co-administered or co-formulated with a proteasome inhibitor. In some such embodiments, the proteasome inhibitor is bortezomib, carfilzomib, MLN9708, or ixazomib.

In some embodiments, a synthetic triterpenoid is administered to reduce the side effects associated with treatment with a proteasome inhibitor. In some such embodiments, the side effects include pain, particularly neuropathic pain. In some such embodiments, the proteasome inhibitor is bortezomib, carfilzomib, MLN9708, or ixazomib.

Bortezomib, which is chemically described as [(1R)-3-methyl-1-[[(2S)-1-oxo-3-phenyl-2-[(pyrazinylcarbonyl)amino]propyl]amino]butyl] boronic acid and available commercially as Velcade™, is a reversible inhibitor of the chymotrypsin-like activity of the 26S proteasome. Bortezomib has been approved to be used in the treatment of various neoplastic diseases, particularly, in the treatment of patients with multiple myeloma and patients with mantle cell lymphoma who have received at least one prior therapy. For multiple myeloma treatment, bortezomib may be, for example, administered subcutaneously or intravenously at a dose of 1.3 mg/m$^2$ once or twice weekly.

Carfilzomib, which is chemically described as (2S)—N—((S)-1-((S)-4-methyl-1-((R)-2-methyloxiran2-yl)-1-oxopentan-2-ylcarbamoyl)-2-phenylethyl)-2-((S)-2-(2-morpholino-acetamido) 4-phenylbutanamido)-4-methylpentanamide and available commercially as Kyprolis™, is an irreversible inhibitor of the 20S proteasome, the proteolytic core particle within the 26S proteasome. Carfilzomib has been approved to be used in the treatment of patients with multiple myeloma who have received at least two prior therapies. For multiple myeloma treatment, carfilzomib may be, for example, administered intravenously at a dose of 20 or 27 mg/m$^2$/day on two consecutive days according to a carfilzomib dosing schedule. An exemplary carfilzomib dosing schedule includes administration on days 1, 2, 8, 9, 15, and 16 of a 28 day cycle.

Ixazomib citrate (MLN9708; Ninlaro®), a prodrug, rapidly hydrolyzes under physiological conditions to its biologically active form, ixazomib. The chemical name of ixazomib citrate is 1,3,2-dioxaborolane-4,4-diacetic acid, 2-[(1R)-1-[[2-[(2,5 dichlorobenzoyl)amino]acetyl]amino]-3-methylbutyl]-5-oxo-. Ixazomib is a reversible inhibitor of the chymotrypsin-like activity of the beta 5 subunit of the 20S proteasome. Ixazomib has been approved to be used in the treatment of patients with multiple myeloma who have received at least one prior therapy. For multiple myeloma treatment, ixazomib may be, for example, administered orally at a dose of 4 mg once weekly according to an ixazomib dosing schedule. An exemplary ixazomib dosing schedule includes administration on days 1, 8, and 15 of a 28 day cycle.

In combination therapy, CDDO-2P-Im or a pharmaceutically acceptable salt thereof may be administered at any suitable frequency and may be administered substantially simultaneous with, or independent from, a proteasome inhibitor. In some embodiments, CDDO-2P-Im or a pharmaceutically acceptable salt thereof is administered at least once daily (e.g., once per day).

CDDO-2P-Im or a pharmaceutically acceptable salt thereof and a proteasome inhibitor may be co-administered to the subject from the same pharmaceutical composition or from separate pharmaceutical compositions. CDDO-2P-Im or a pharmaceutically acceptable salt thereof and a proteasome inhibitor may be co-administered in a substantially simultaneous manner (e.g., within about 5 min of each other), in a sequential manner, or both. It is contemplated, for example, that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient.

CDDO-2P-Im or a pharmaceutically acceptable salt thereof and a proteasome inhibitor may be co-administered with one or more additional therapeutic agents in the same or separate pharmaceutical compositions. Such therapeutic agents may include other therapeutic agents used to treat cancer. For example, CDDO-2P-Im or a pharmaceutically acceptable salt thereof and a proteasome inhibitor may be co-administered with an immunomodulatory agent and/or a corticosteroid. Exemplary immunomodulatory agents include, but are not limited to, thalidomide, lenalidomide, and pomalidomide. Thalidomide, which is chemically described as 3-(4-amino-1-oxo 1,3-dihydro-2H-isoindol-2-yl) piperidine-2,6-dione and available commercially as Revlimid®. Lenalidomide, which is chemically described as α-(N-phthalimido) glutarimide and available commercially as Thalomid®. Pomalidomide, which is chemically described as (RS)-4-Amino-2-(2,6-dioxopiperidin-3-yl)-isoindoline-1,3-dione and available commercially as Pomalyst®. Exemplary corticosteroids include, but are not limited to, dexamethasone and prednisone.

For multiple myeloma treatment, thalidomide may be, for example, administered orally at a dose of 200 mg once daily. For multiple myeloma treatment, lenalidomide may be, for example, administered orally at a dose of 10 or 25 mg once daily. For multiple myeloma treatment, pomalidomide may be, for example, administered orally at a dose of 4 mg per day. For multiple myeloma treatment, dexamethasone may be, for example, administered at a dose of 20 or 40 mg/day on according to a dexamethasone dosing schedule. An exemplary dexamethasone dosing schedule includes administration on days 1, 8, 15, and 22 of a 28 day cycle. Alternatively, an exemplary dexamethasone dosing schedule includes administration on days 1-4, 9-12, and 17-20, of a 28 day cycle.

2. Use in Brain Cancer Treatment

In one aspect, this disclosure provides a synthetic triterpenoid, such as CDDO-2P-Im, CDDO-3P-Im, or a pharmaceutically acceptable salt thereof, for use as a single agent or in combination with one or more additional therapeutic agents (e.g., an oral chemotherapeutic agent, such as an alkylating agent like temozolomide) in a method of treating a solid tumor and particularly a brain tumor. In such aspects, a synthetic triterpenoid is administered to a patient to treat a solid tumor and particularly a brain tumor. In some embodiments, the synthetic triterpenoid is CDDO-2P-Im or a pharmaceutically acceptable salt thereof. In some embodiments, CDDO-2P-Im or a pharmaceutically acceptable salt thereof is co-administered with one or more therapeutic agents to treat a solid tumor and particularly a brain tumor.

In some embodiments, a synthetic triterpenoid is co-administered or co-formulated with an oral chemotherapeutic agent. In some such embodiments, the oral chemotherapeutic agent is an alkylating agent. In some such embodiments, the alkylating agent is temozolomide.

In some embodiments, a synthetic triterpenoid is administered to reduce the side effects associated with treatment with an oral chemotherapeutic agent. In some such embodiments, the side effects include lymphopenia. In some such embodiments, the oral chemotherapeutic agent is an alkylating agent. In some such embodiments, the alkylating agent is temozolomide.

Temozolomide, which is chemically described as 3,4-dihydro-3-methyl-4-oxoimidazo[5,1-d]-as-tetrazine-8-carboxamide and available commercially as Temodar®, is an alkylating agent. Temozolomide has been approved to be used in the treatment of adult patients with (1) newly diagnosed glioblastoma multiforme concomitantly with radiotherapy and then as maintenance treatment and (2) refractory anaplastic astrocytoma patients who have experienced disease progression on a drug regimen containing nitrosourea and procarbazine. For GBM treatment, temozolomide may be, for example, administered orally (or intravenously) at a dose of 75 mg/m$^2$ daily and, preferably, concomitant with radiotherapy. Temozolomide may also be administered (e.g., during a maintenance phase) or orally (or intravenously) at a dose of 150 or 200 mg/m$^2$ once daily according to a temozolomide maintenance phase dosing schedule. An exemplary temozolomide maintenance phase dosing schedule includes administration on days 1-5 of a 28 day cycle.

In combination therapy, CDDO-2P-Im or a pharmaceutically acceptable salt thereof may be administered at any suitable frequency and may be administered substantially simultaneous with, or independent from, an oral chemotherapeutic agent. In some embodiments, CDDO-2P-Im or a pharmaceutically acceptable salt thereof is administered at least once daily (e.g., once per day).

CDDO-2P-Im or a pharmaceutically acceptable salt thereof and an oral chemotherapeutic agent may be co-administered to the subject from the same pharmaceutical composition or from separate pharmaceutical compositions. CDDO-2P-Im or a pharmaceutically acceptable salt thereof and an oral chemotherapeutic agent may be co-administered in a substantially simultaneous manner (e.g., within about 5 min of each other), in a sequential manner, or both. It is contemplated, for example, that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient.

CDDO-2P-Im or a pharmaceutically acceptable salt thereof and an oral chemotherapeutic agent may be co-administered with one or more additional therapeutic agents in the same or separate pharmaceutical compositions. Such therapeutic agents may include other therapeutic agents used to treat cancer.

3. Use in Solid Tumor Treatment

In one aspect, this disclosure provides a synthetic triterpenoid, such as CDDO-2P-Im, CDDO-3P-Im, or a pharmaceutically acceptable salt thereof, for use as a single agent or in combination with one or more additional therapeutic agents (e.g., an injectable chemotherapeutic agent, such as a platinum compound like cisplatin) in a method of treating a solid tumor, such as an ovarian tumor. In such aspects, a synthetic triterpenoid is administered to a patient to treat a solid tumor, such as an ovarian tumor. In some embodiments, the synthetic triterpenoid is CDDO-2P-Im or a pharmaceutically acceptable salt thereof. In some embodiments, CDDO-2P-Im or a pharmaceutically acceptable salt thereof is co-administered with one or more therapeutic agents to treat the solid tumor.

In some embodiments, a synthetic triterpenoid is co-administered or co-formulated with an injectable chemotherapeutic agent. In some such embodiments, the injectable chemotherapeutic agent is a platinum compound. The term "platinum compound" refers to compounds containing platinum in their structure such as platinum complexes and includes compounds such as cisplatin, carboplatin and oxaliplatin. In particular, cisplatin is chemically described as cis-diamminedichloroplatinum(II) (CDDP) and has following formula:

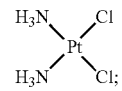

carboplatin is chemically described as platinum, diammine [1,1-cyclobutanedicarboxylato(2-)—O,O']—, (SP-4-2) and has following formula:

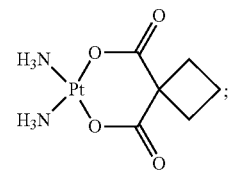

and oxaliplatin is chemically described cis-[(1R,2R)-1,2-cyclohexanediamine-N,N'] [oxalato(2-)—O,O'] platinum and has following formula:

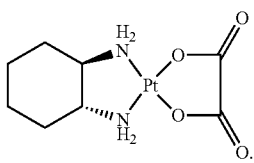

Cisplatin for injection is available commercially as Platinol®. For treatment of ovarian tumors, cisplatin may be, for example, administered intravenously at a dose of 75 to 100 mg/m² once every four weeks.

Carboplatin is available commercially as Paraplatin®. For treatment of ovarian tumors, cisplatin may be, for example, administered intravenously at a dose of 300 to 360 mg/m² once every four weeks.

Oxaliplatin for injection is also marketed under the trade name Eloxatin®. For treatment of colon or colorectal tumors, oxaliplatin may be, for example, administered intravenously at a dose of 85 mg/m² once every two weeks.

In combination therapy, CDDO-2P-Im or a pharmaceutically acceptable salt thereof may be administered at any suitable frequency and may be administered substantially simultaneous with, or independent from, an injectable chemotherapeutic agent. In some embodiments, CDDO-2P-Im or a pharmaceutically acceptable salt thereof is administered at least once daily (e.g., once per day).

CDDO-2P-Im or a pharmaceutically acceptable salt thereof and an injectable chemotherapeutic agent may be co-administered with one or more additional therapeutic agents in the same or separate pharmaceutical compositions. Such therapeutic agents may include other therapeutic agents used to treat cancer. For example, CDDO-2P-Im or a pharmaceutically acceptable salt thereof and an injectable chemotherapeutic agent (e.g., a platinum compound) may be co-administered with cyclophosphamide, which is chemically described as 2-[bis(2-chloroethyl)amino]tetrahydro-2H-1,3,2-oxazaphosphorine 2-oxide monohydrate. In combination with a platinum compound, cyclophosphamide may be, for example, administered intravenously at a dose of 600 mg/m² once every four weeks.

In some embodiments, a synthetic triterpenoid, such as CDDO-2P-Im, is co-administered to a patient with a platinum compound-containing combination to treat a solid tumor. Such platinum compound-containing combinations may be a combination used in a chemotherapeutic regimen selected from the group consisting of EOX chemotherapy, ECF chemotherapy, ECX chemotherapy, EOF chemotherapy, FLO chemotherapy, FOLFOX chemotherapy, DCF chemotherapy and FLOT chemotherapy. The drug combination used in EOX chemotherapy comprises epirubicin, oxaliplatin, and capecitabine. The drug combination used in ECF chemotherapy comprises epirubicin, cisplatin, and 5-fluorouracil. The drug combination used in ECX chemotherapy comprises epirubicin, cisplatin, and capecitabine. The drug combination used in EOF chemotherapy comprises epirubicin, oxaliplatin, and 5-fluorouracil. The drug combination used in FLO chemotherapy comprises 5-fluorouracil, folinic acid, and oxaliplatin. The drug combination used in FOLFOX chemotherapy comprises folinic acid (leucovorin), 5-fluorouracil, and oxaliplatin. The drug combination used in DCF chemotherapy comprises docetaxel, cisplatin, and 5-fluorouracil. The drug combination used in FLOT chemotherapy comprises of docetaxel, oxaliplatin, 5-fluorouracil, and folinic acid.

D. EXAMPLES

Example 1: Blood Cancer

A well-characterized syngeneic model of MM was employed. Adoptive transfer of 5T33MM cells into C57BL/KaLwRij recipient mice invariably leads to MM bone disease, impaired hematopoietic function and death. This is an elegant model that faithfully recapitulates all aspects of the human features of MM and it has recently been utilized to show that myeloma cells act to induce Mcl-1 expression and promote survival of myeloid derived suppressor cells (MDSCs) in the tumor microenvironment (TME).

To monitor MM tumor progression in the 5T33MM preclinical model, a 5T33MM cell line that expresses either luciferase or GFP genes was established by transducing with lentiviral particles containing firefly luciferase and GFP genes (Amsibo, Cambridge, MA); cells were selected with FACS sorting for GFP expression and by puromycin-resistance. For these experiments, 1×10⁶ 5T33MM-luc cells were introduced by intravenous injection into C57BL/KaLwRij mice at 2 months of age. Bioluminescence (BLI) was measured by using the IVIS Imaging System 100 (Xenogen). At 3 weeks after 5T33MM cell inoculation (where mice have established disease by BLI), mice were randomized to receive either vehicle, CDDO-2P-IM (0.5 μmole/310 mg daily administered by oral gavage (po), 5 days/week), or ixazomib (IXZ; 6 mg/kg per week, administered po every Monday, Wednesday and Friday). The results of this initial experiment establish that CDDO-2P-IM is: a) well tolerated given in a daily oral regimen; b) active against MM in an immune competent model; and c) effective as a single agent with anti-MM activity that is either comparable to or better than IXZ (see FIG. 1). CDDO-2P-IM to exhibits significant activity when administered as a single agent, compared to the FDA-approved proteasome inhibitor ixazomib (IXZ).

Figure 2:
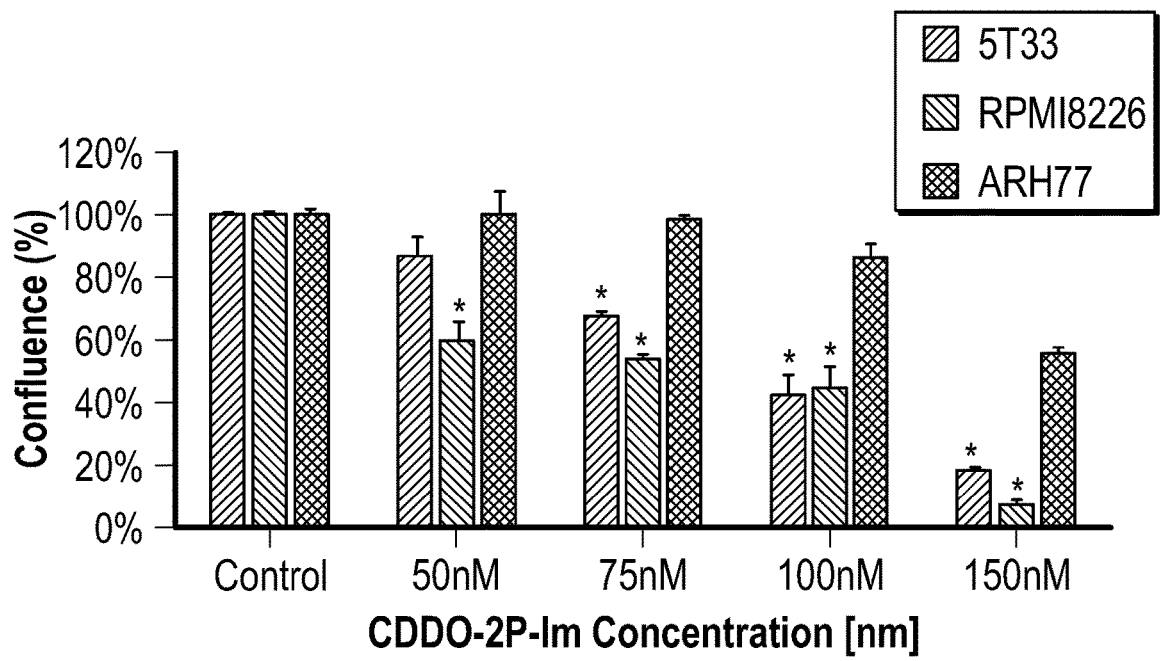
FIG. 2 is a bar graph. CDDO-2P-Im inhibits proliferation of multiple myeloma cell line in vitro. 5T33MM, RPMI8226, and ARH77 cells were seeded in 96-well plates and incubated with CDDO-2P-Im (50 nM-150 nM). Confluence (cell proliferation) was measured using IncuCyte imaging after 72 hours. *p<0.01 compared to control.
Figure 3:
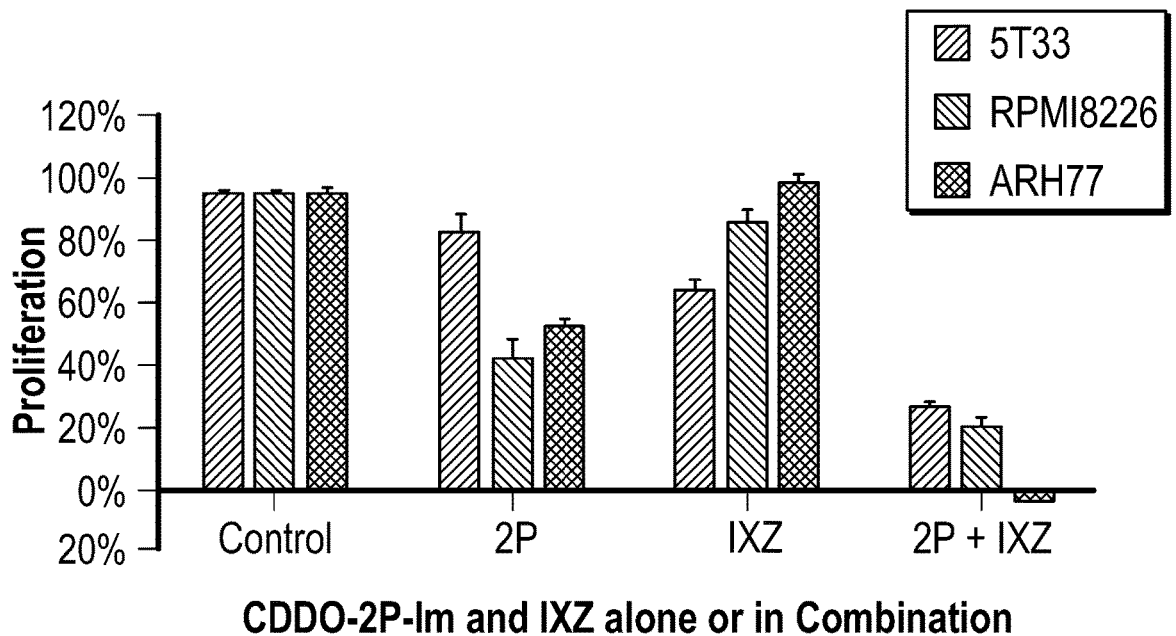
FIG. 3 is a bar graph. CDDO-2P-Im and ixazomib (IXZ) act synergistically to suppress proliferation of mouse and human myeloma cells in vitro. 5T33MM, RPMI8226, and ARH77 cells were incubated with distinct concentrations of CDDO-2P-Im and IXZ that are only partially effective when added alone to MM cells in culture. Shown here are results for 5T33MM (50 nM TTX01/7.5 nM IXZ); RPMI8226 (100 nM TTX01/7.5 nM IXZ); and ARH77 (150 nM TTX01/10 nM IXZ). Confluence (cell proliferation) was measured using IncuCyte imaging after 72 hours.

To examine tumor-intrinsic effects of CDDO-2P-IM in the 5T33MM cell line and in human MM cells, conducted a series of in vitro studies was conducted. For these experiments, 96-well plates were first coated in poly-L-ornithine before cells were seeded (in triplicate), including the murine 5T33MM and the human RPMI8226, and ARH77 cell lines (15,000 cells per well). Cells were incubated in IncuCyte™ Live-Cell Analysis System for 72 hours (images were taken every 4 hours). To define dose-dependent effect of CDDO-2P-IM, cells were exposed to concentrations ranging from 50 nM to 150 nM. To examine potential synergy of CDDO-2P-IM with IXZ, MM cells were exposed to IXZ (7 nM-10 nM) either alone or in combination with CDDO-2P-IM. The data (FIG. 2) reveal significant dose-dependent suppressive effects of CDDO-2P-IM on the proliferation of MM cells in culture at concentrations that are readily achieve in vivo. More importantly, in vitro exposure of both murine and human MM cells to the combination of CDDO-2P-IM and IXZ at doses that are suboptimal for each agent alone reveals a remarkable synergy of the combination of CDDO-2P-IM and IXZ (FIG. 3).

Data presented herein show that CDDO-2P-Im strongly suppresses patient-derived multiple myeloma (MM) cell lines and shows robust synergy when combined with ixazomib (IXZ) in cultures of MM cells.

Example 2: Inflammasome Activity

Example 2.1

Figure 4A:
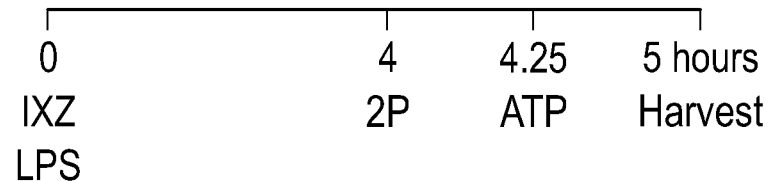
FIG. 4A depicts an experimental design and FIG. 4B is a bar graph. Ixazomib (IXZ) potentiation of NLRP3 inflammasome activation inhibited by CDDO-2P-Im. Bone marrow derived macrophages (BMDM) were treated with Ixazomib (IXZ) and LPS (100 ng/ml) for 20 hours. Primed-BMDM were treated with CDDO-2P-Im (100 nM) for 15 min, followed by stimulation of ATP (5 mM) for 45 min. Supernatant were analyzed by ELISA for IL-1β release.
Figure 4B:
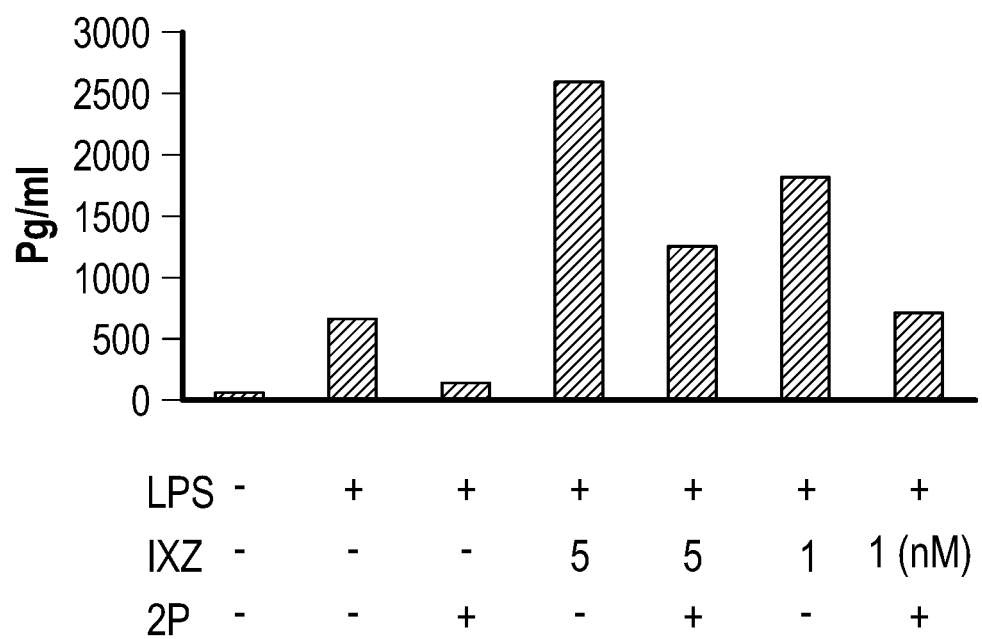

To explore the potential that CDDO-2P-IM may enhance the MM response to proteasome inhibitors via inhibition of inflammasome activity, the effect of CDDO-2P-IM on activation of the NLRP3 complex (as defined by IL-1β production), in the presence or absence of IXZ in primary mouse bone marrow derived macrophages (BMDM) was evaluated. In the experiment, BMDM were primed by lipopolysaccharide (LPS) in the presence or absence of IXZ for 4 hours, followed by a brief (25 min) exposure to CDDO-2P-IM after which inflammasome activation was triggered by ATP. The analyses of IL-1β secretion (FIG. 4) not only show the profound amplification of inflammasome activity induced by ATP and to also significantly reduce the impact of IXZ on inflammasome activation.

These studies have revealed: a) profound single agent anti-myeloma activity of CDDO-2P-IM; b) significant synergy between CDDO-2P-IM and IXZ (an FDA-approved therapy for MM); and c) direct suppression of NLRP3 inflammasome activation and abrogation of the enhancement of inflammasome activity by IXZ.

Example 2.2

Figure 5:
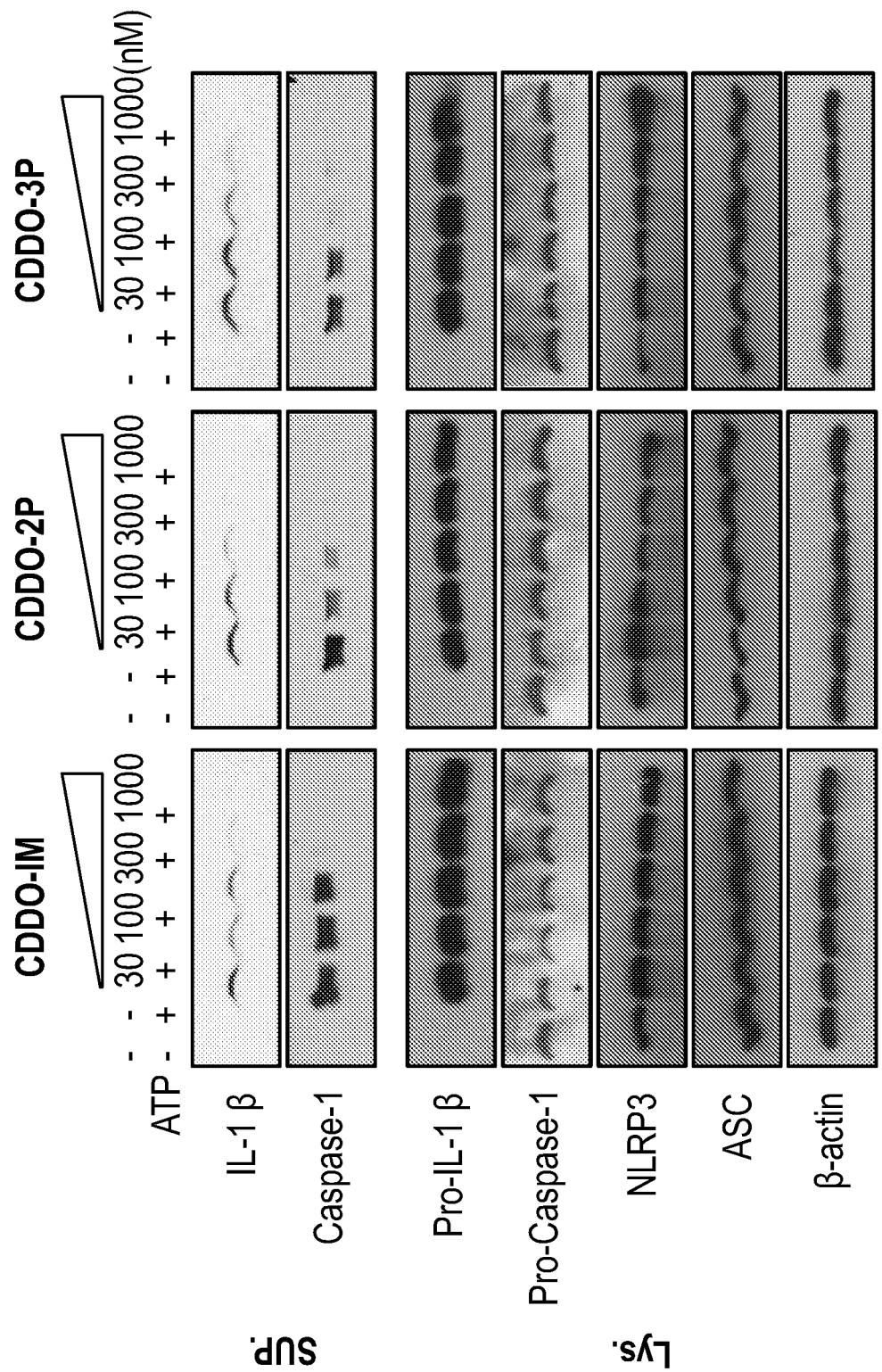
FIG. 5 depicts a Western blot. CDDO-Im, CDDO-2P-Im, and CDDO-3P-Im inhibit Caspase 1 activation. LPS primed BMDM were treated with different doses of CDDO-Im, CDDO-2P-Im, or CDDO-3P-Im for 15 min before ATP (5 mM) was added for 45 min. Medium supernatant (SUP) and cell extracts (Lys) were analyzed by immunoblotting.
Figure 6:
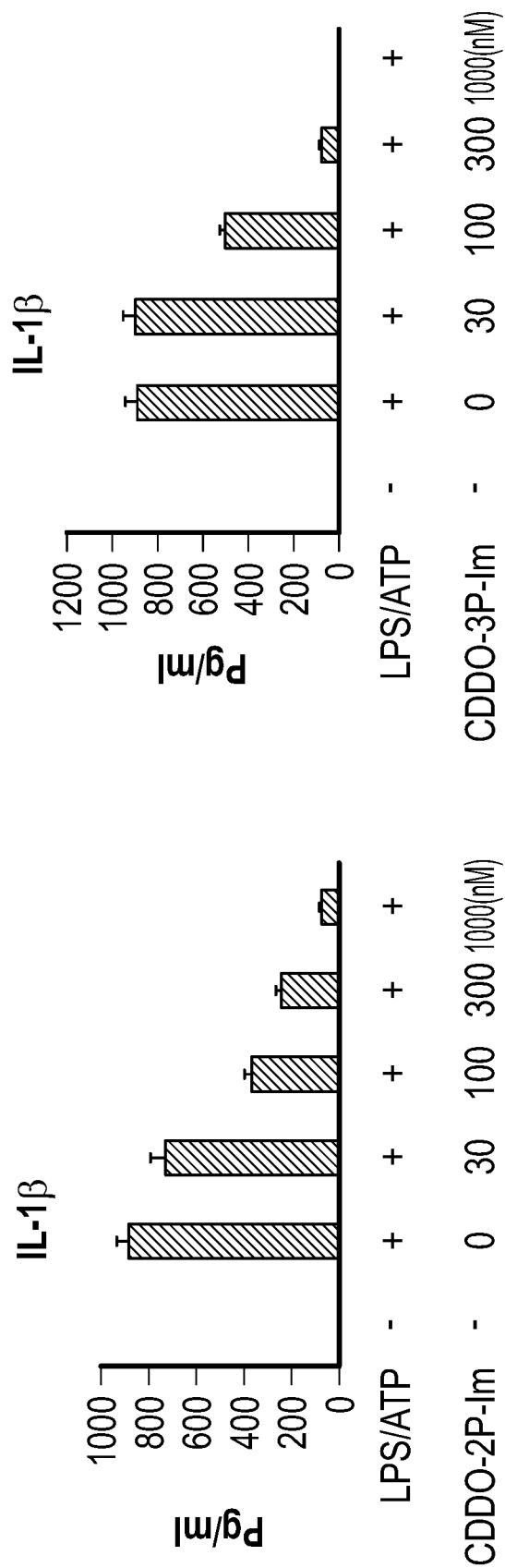
FIG. 6 is a set of bar graphs. CDDO-Im, CDDO-2P-Im (right panel), and CDDO-3P-Im (left panel) inhibit IL-1β production by NLRP3 inflammasome activation. LPS primed-BMDM were treated with different doses of CDDO-Im, CDDO-2P-Im, or CDDO-3P-Im for 15 min before ATP (5 mM) was added for 45 min. Supernatant were analyzed by ELISA for IL-1β.

The effects of the pyridyl derivatives of CDDO-IM, (specifically, CDDO-2P-Im and CDDO-3P-Im) on NLRP3 inflammasome activation were tested in mouse BMDMs. Cells were first primed with LPS for 4 hours, then pretreated with specific doses of either CDDO-Im, CDDO-2P-IM or CDDO-3P-Im (30-1000 nM) for 15 min before ATP was added for another 45 min. CDDO-Im and its pyridyl derivatives inhibited the amount of caspase-p10 (an auto-processed fragment of caspase-1) released into cell culture supernatants in a dose-dependent manner as measured by Western blot (FIG. 5). This brief exposure to the selected synthetic triterpenoids also prevented secretion of the caspase-1 dependent cytokine IL-1β into media, as measured by ELISA (see FIG. 6). The effect on caspase-1 activation is specific for the NLRP3 inflammasome as the AIM2 inflammasome activation by poly(dA:dT) was not inhibited by the synthetic CDDO-Im derivatives (data not shown).

Example 2.3

Figure 7:
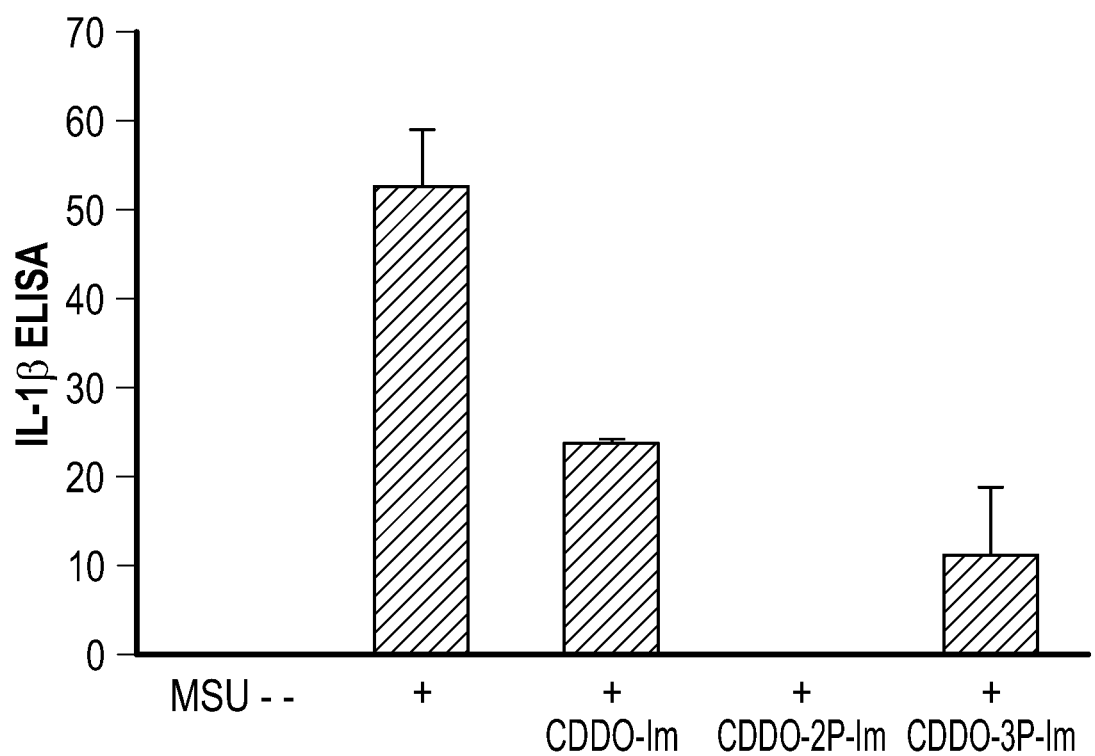
FIG. 7 is a bar graph. CDDO-Im, CDDO-2P-Im, and CDDO-3P-Im inhibit mono-sodium urate (MSU)-induced peritonitis. Peritoneal cavity IL-1β levels expressed as mean and SEM (n=6).

Mice received intraperitoneal (i.p.) injections of monosodium urate (MSU) crystals (1 mg/mouse) in the presence or absence of CDDO-Im, CDDO-2P-Im, or CDDO-3P-Im. Due to its particulate material, MSU crystals are potent activators of the NOD-like receptor NLRP3. Four to sixteen hours later a peritoneal lavage was conducted to collect supernatant from the peritoneal cavity. As shown in FIG. 7, CDDO-Im, CDDO-2P-Im, and CDDO-3P-Im inhibit MSU-induced peritonitis.

Data presented herein show that CDDO-2P-Im potently inhibits inflammasome activity, which is believed to be, among other things, a cause of major pain in MM.

The data presented in Examples 1 and 2 support the potential for CDDO-2P-Im to augment the current standard of care for patients with MM, with an opportunity to significantly reduce the risks associated with chronic exposure to PIs, including painful neuropathy.

Example 3: Brain Tumors

Example 3.1

To define the capacity of CDDO-2P-IM to suppress the growth and viability of GBM, several well-characterized human GBM cell lines (U251, U-87MG, LN227, Gli36Δ5), primary cultures of patient-derived GBM cells (UVM04, D028), and normal human astrocytes (provided by Dr. Arti Gaur, Dartmouth College) were utilized. The in vitro dose-dependent effects of CDDO-2P-IM alone and in combination with TMZ were demonstrated.

Figure 8:
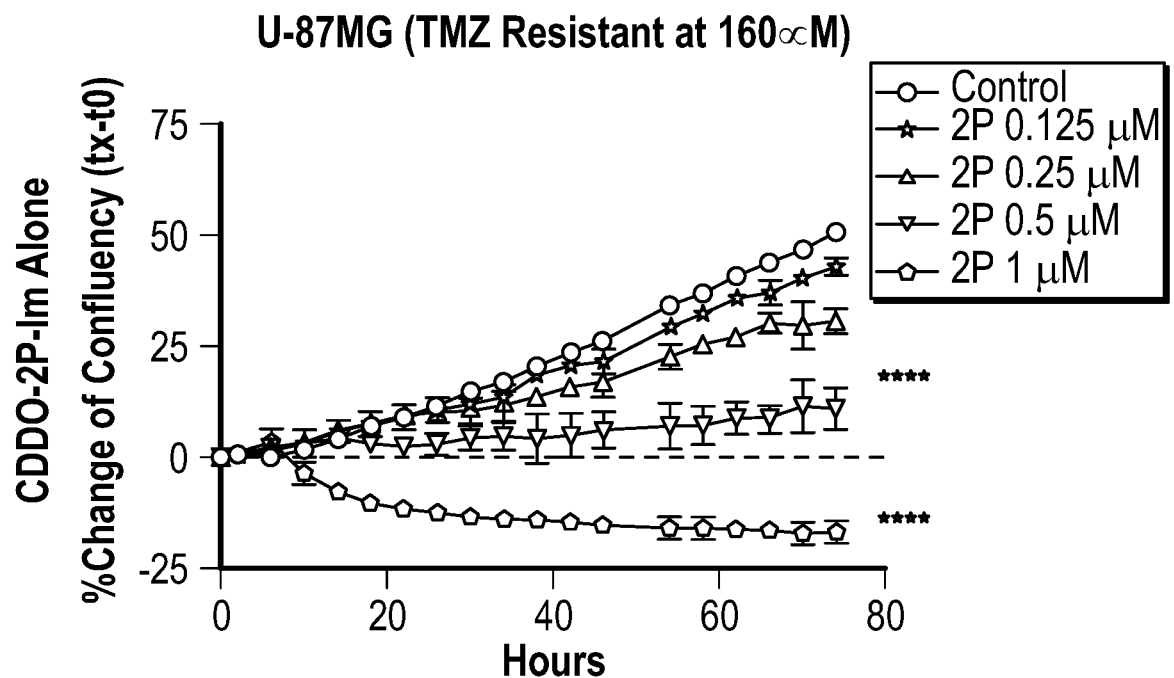
FIG. 8 is a set of line graphs. CDDO-2P-Im suppresses growth of TMZ-resistant human GBM cells in vitro. Exposure of GBM lines U-87MG (left panels) and LN227 (right panels) to CDDO-2P-Im suppressed growth in a dose-dependent manner at nanomolar (nM) concentrations, defined by confluence assessed in the Incucyte® system. Reduction in confluence is accompanied by the detachment and death of GBM cells. The data reveal that the relatively TMZ-resistant U-87MG is equivalent to LN227 in its sensitivity to CDDO-2P-Im. Moreover, a significant gain in GBM cell kill is observed when a suboptimal does of CDDO-2P-Im combined with a TMZ dose that alone has absolutely no effect in U-87MG cells (bottom left panel; significance at 0.005 or greater).
Figure 8:
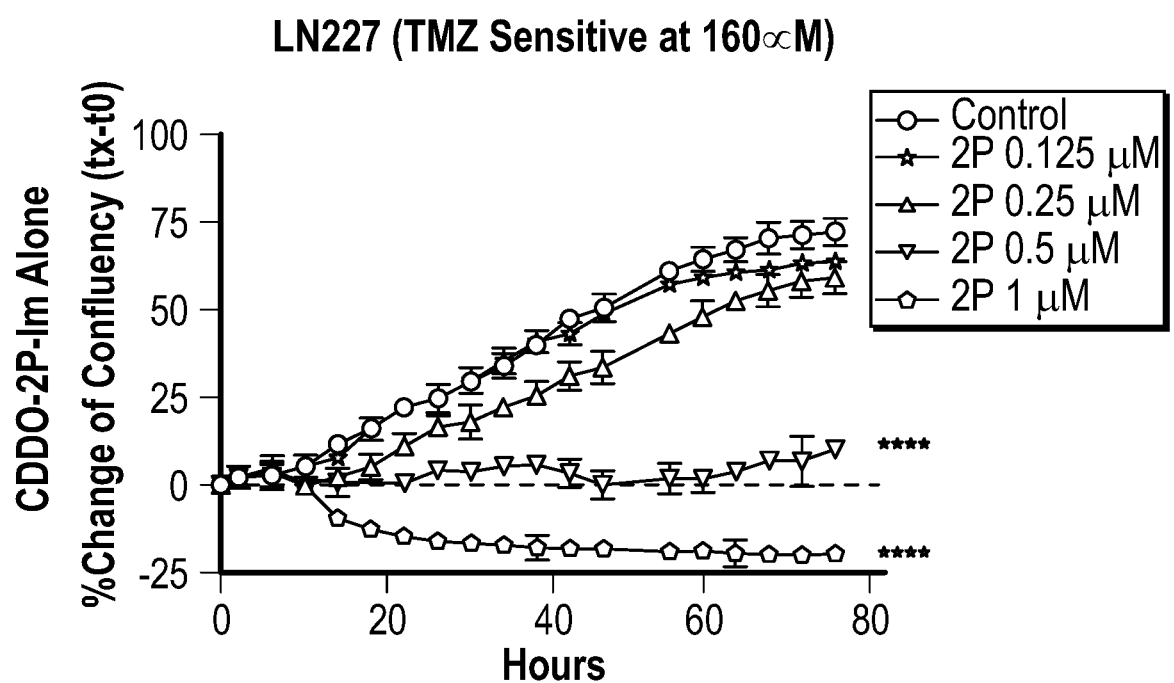
Figure 8:
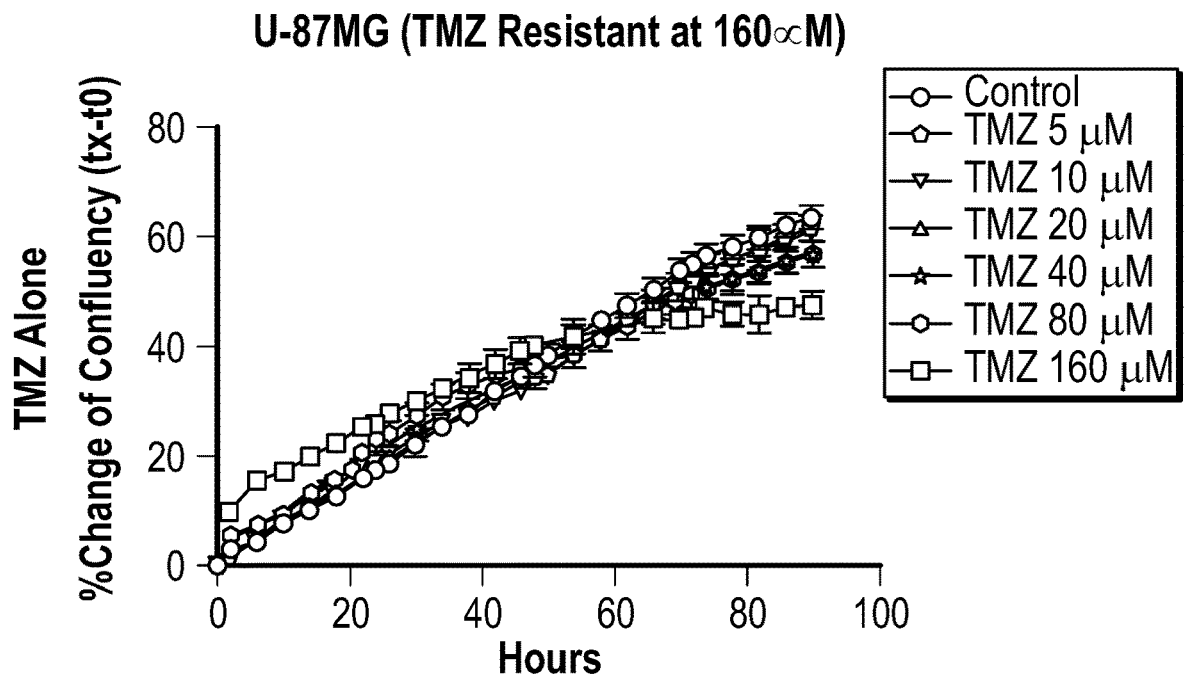
Figure 8:
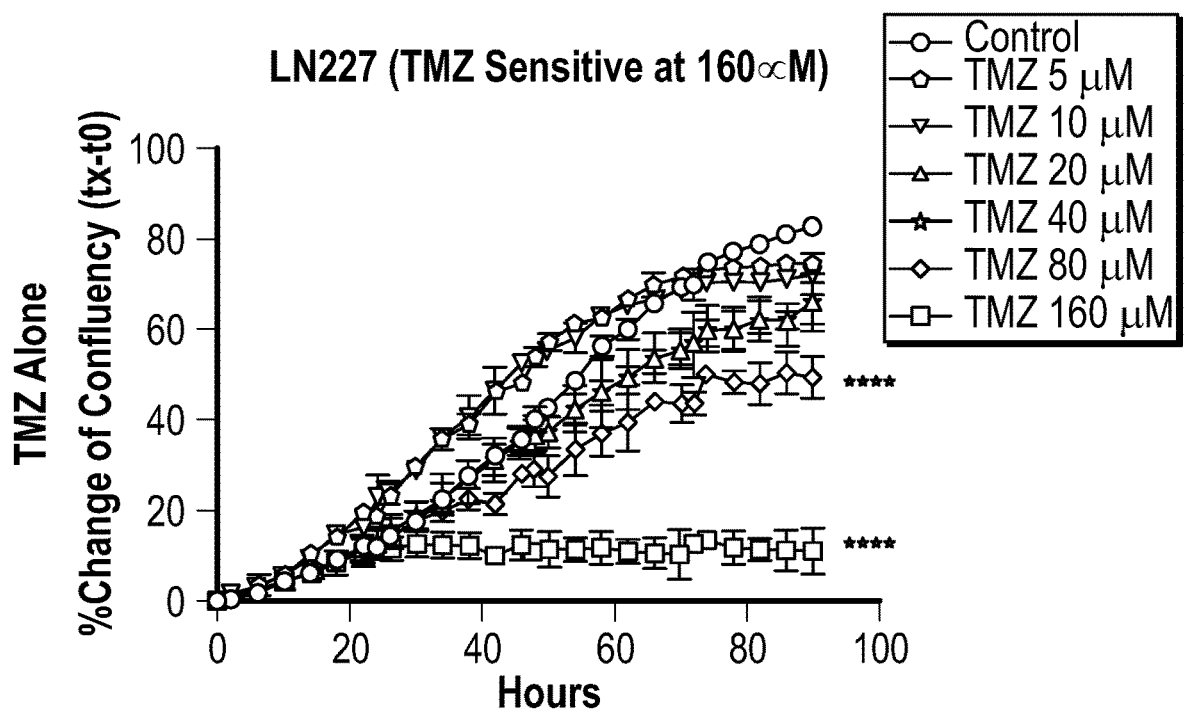
Figure 8:
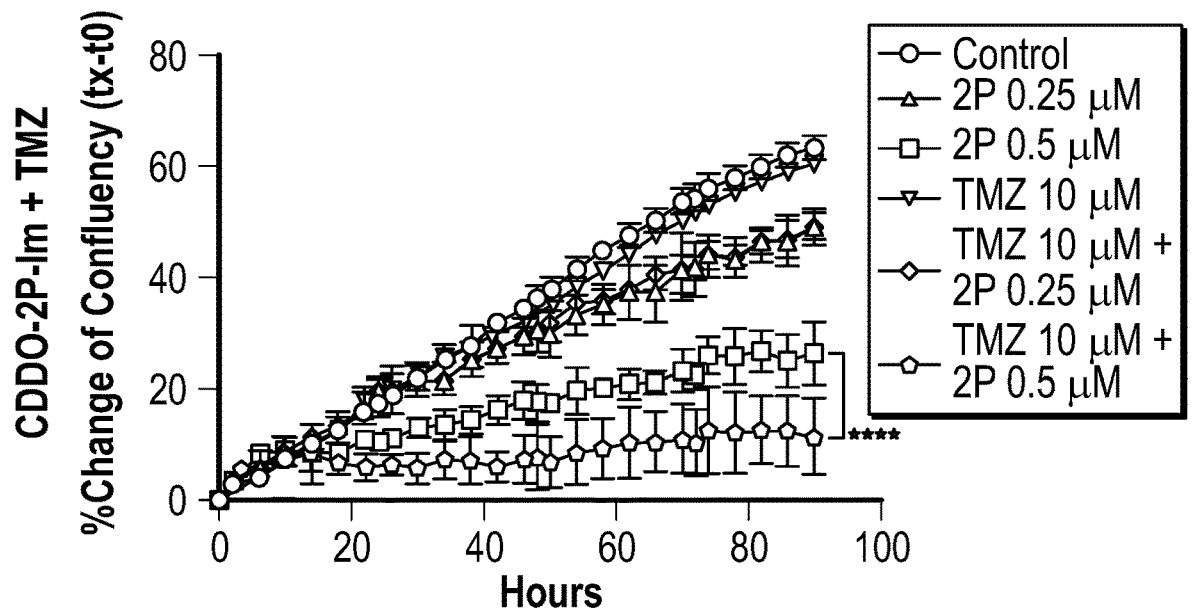
Figure 8:
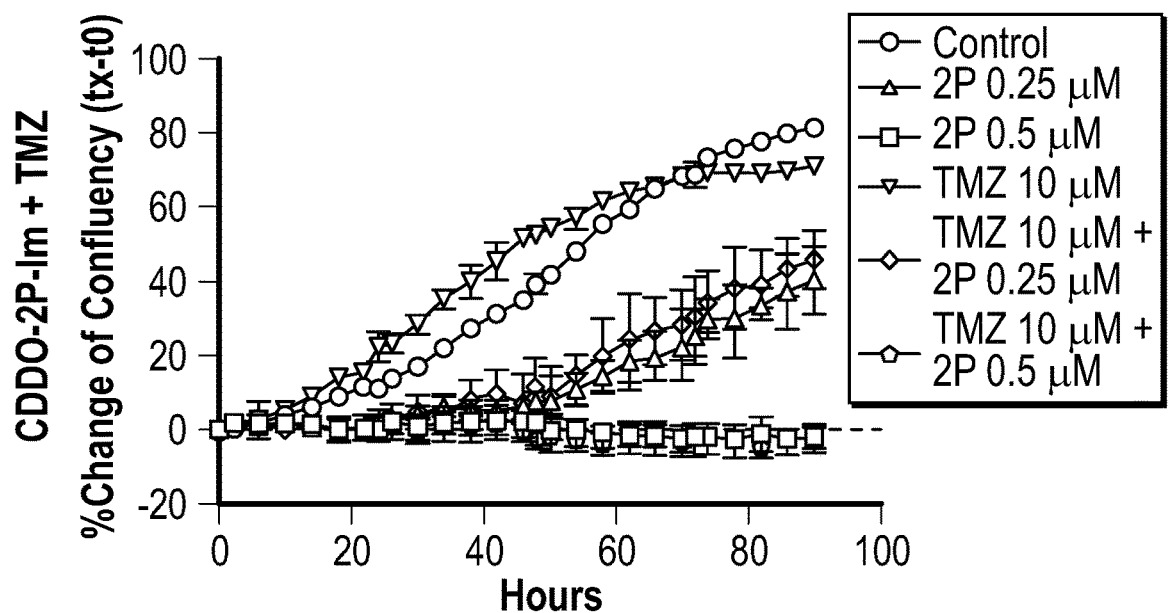

CDDO-2P-IM is significantly more potent than TMZ in the suppression of human GBM cell viability in vitro. The activity of CDDO-2P-IM in cultures of human GBM was assessed and similar nanomolar (nM) potency was observed. Utilizing the IncuCyte® System (Sartorius), a dose-dependent reduction in the confluence of established cell lines U-87-MG, LN227 (FIG. 8) and U251, (not shown), well below concentrations of TMZ required to suppress the growth of either cell line (see TMZ alone middle panels FIG. 8) was observed. These changes in confluence observed by Incucyte® corresponded with a reduction in cell viability. Doses of CDDO-2P-IM that result in complete cell death of the LN227, U251 and U-87MG cell lines had no effect on the viability of primary human astrocytes in vitro (not shown). Similar results were observed in primary cultures of human GBM in which a significant reduction in cell viability was observed at concentrations below 100 nM.

CDDO-2P-Im suppresses the growth of brain tumor cell lines in vitro and enhances radiation response in these cell lines in vitro.

These data demonstrate that CDDO-2P-Im has potential to directly suppress growth tumor growth, enhance tumor response to radiation therapy, and reduce development of radiation-induced toxicity.

Data presented herein show that CDDO-2P-Im significantly reduces viability in primary cultures of patient-derived GBM cells and of GBM cell lines in vitro at nanomolar concentrations, with no effect on the growth and viability of normal astrocytes.

Data presented herein show that CDDO-2P-Im suppresses growth of TMZ-resistant GBM cells in vitro. Moreover, a significant gain in GBM cell kill was observed when a suboptimal dose of CDDO-2P-Im was combined with a TMZ dose that alone had no effect in TMZ-resistant GBM cells.

Figure 9:
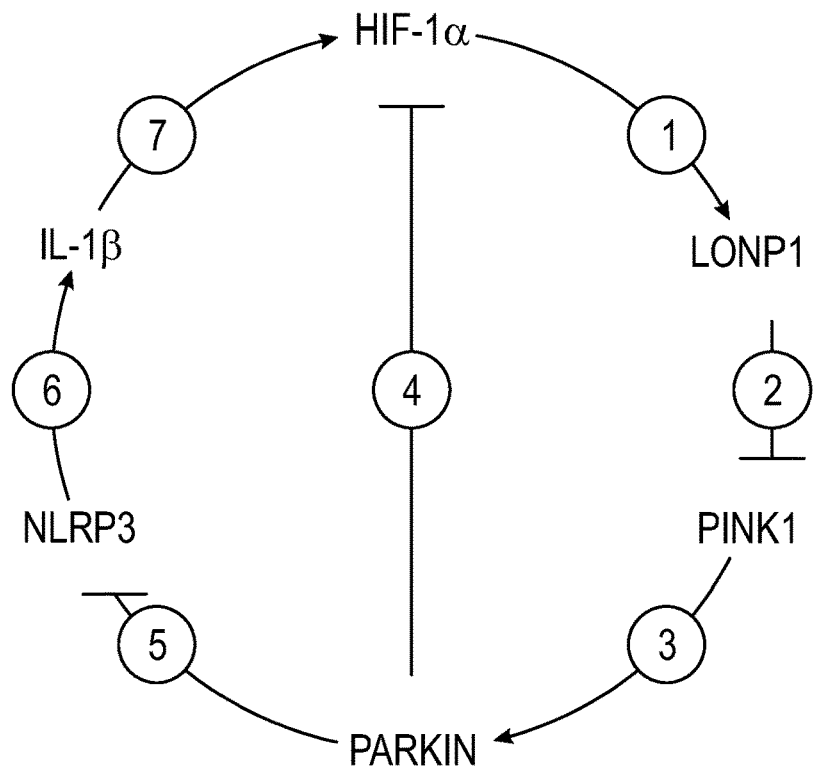
FIG. 9 is a schematic representation of a vicious cycle involving defective mitochondrial function linking LON protease (LONP1) to defects in mitophagy and to the production of inflammatory mediators in the tumor microenvironment (TME).

LONP1 has been identified as a target for CDDO-2P-Im and CDDO-2P-Im has been shown to bind LONP1. Without wishing to be bound by theory, it is believed that direct binding of CDDO-2P-Im to LONP1 is a key mechanism that underlies suppression of GBM cell viability by CDDO-2P-Im and inhibition of the inflammasome by CDDO-2P-Im. CDDO-2P-Im may act by promoting activity of the PINK1/Parkin complex, located on the mitochondrial membrane (see FIG. 9). The hypoxic tumor microenvironment (TME) and the inflammatory cytokine IL-1β activate the Lon protease (LONP1) via HIF1α. Chemotherapy, including temozolomide (TMZ), and radiation therapy both rapidly induce expression of LONP1. LON protease degraded the PINK1 kinase, negatively regulating the activity of the PINK1/Parkin complex. PINK1 recruits Parkin to the outer mitochondrial membrane and activates Parkin's E3 ubiquitin ligase function via phosphorylation. Parkin ubiquitinates HIF1α, thereby negatively regulating LONP1 induction. Parkin prevents activation of the NLRP3 inflammasome through induction of mitophagy and via enhanced expression of the regulatory protein A20 which restrains NFκB induced expression of NLRP3. The NLRP3 inflammasome is activated by chemotherapy and radiation therapy, leading to activation of IL-1β through induction of caspase 1 activity. The inflammatory cytokine IL-1β activated HIF1α, which upregulateds LONP1. LONP1 is a direct target of CDDO-2P-Im, and inhibition of LONP1 by CDDO-2P-Im breaks this cycle, enhancing PINK/PARKIN regulation of inflammasome activation.

Example 3.2

The CC chemokine, CCL2 (previously named MCP-1), has been implicated in tumor immune evasion through recruitment of immunosuppressive regulatory T cells and/or myeloid-derived suppressor cells. Macrophages and microglia within the glioma microenvironment produce CCL2 and in clinical specimens of GBM, elevated levels of CCL2 expression correlated with reduced overall survival of patients. See Chang et al., Cancer Res. 76(19):5671-5682 (2016).

Human peripheral blood monocytes were isolated using CD14 magnetic beads and differentiated with 20 ng/ml M-CSF for with 5 days and pretreated or not with 300 nM CDDO-Me; 500 pM CDDO-Im; 500 pM CDDO-2p-Im; 500 pM CDDO-3p-Im for 16 hours, followed by stimulation with 10 ng/ml LPS for an additional 24 hours. Total RNA was extracted and analyzed by RT-qPCR (Tagman) for cytokine expression.

Figure 10:
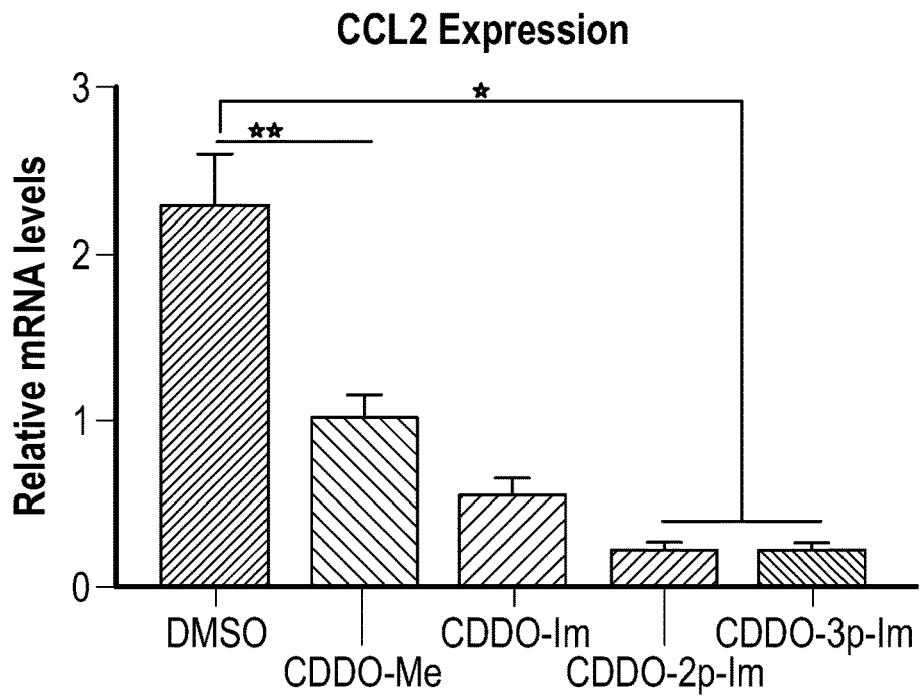
FIG. 10 is a bar graph. CDDO-Me, CDDO-Im, CDDO-2P-Im, and CDDO-3P-Im inhibit expression of CCL2 in human macrophages at picomolar concentrations.

As shown in FIG. 10, CDDO-imidazolides, including CDDO-2P-Im, suppress production of CCL2 by human peripheral blood monocytes at picomolar concentrations.

These data demonstrating potent suppression of CCL2 production by human peripheral blood monocytes further supports the clinical application of CDDO-2P-Im in GBM.

Example 3.3

Mice (3 per group) were treated with single intraperitoneal (i.p.) doses of either 1 micromole (low dose) or 2 micromoles (high dose) of CDDO-2P-Im in DMSO. Brains were analyzed either 3 or 6 hours after dosing. Brains were homogenized in saline, then extracted with acetonitrile, and the extracts subjected to HPLC/Mass Spec analysis, using appropriate standard curves from spiked homogenates. Values obtained (in nanomoles/kg of brain) were: 270+/−80 (low dose, 3 hours); 300+/−90 (low dose, 6 hours); 2,600+/−2,200 (high dose, 3 hours); and 540+/−260 (high dose, 6 hours). Oral dosing of 1 micromole of CDDO-2P-Im in DMSO gave similar results at 6 hours.

A second experiment with oral or i.p. dosing of 1 micromole of CDDO-2P-Im, and analysis at 6 hours, confirmed the above results, with drug levels in brain ranging from 140 to 900 nanomoles/kg of brain in 10 different samples from cerebral cortex.

Data presented herein show significant levels of CDDO-2P-Im in brain after systemic dosing. Previous data (shown above) demonstrate that these concentrations of CDDO-2P-Im kill essentially all cells in cultures derived from human GBM.

These data presented in Example 3 support the potential for CDDO-2P-Im to augment the current standard of care for patients with GBM (TMZ and radiation therapy), and to reduce the risks associated with chronic exposure to TMZ.

Example 4: Ovarian Tumors

Figure 11:
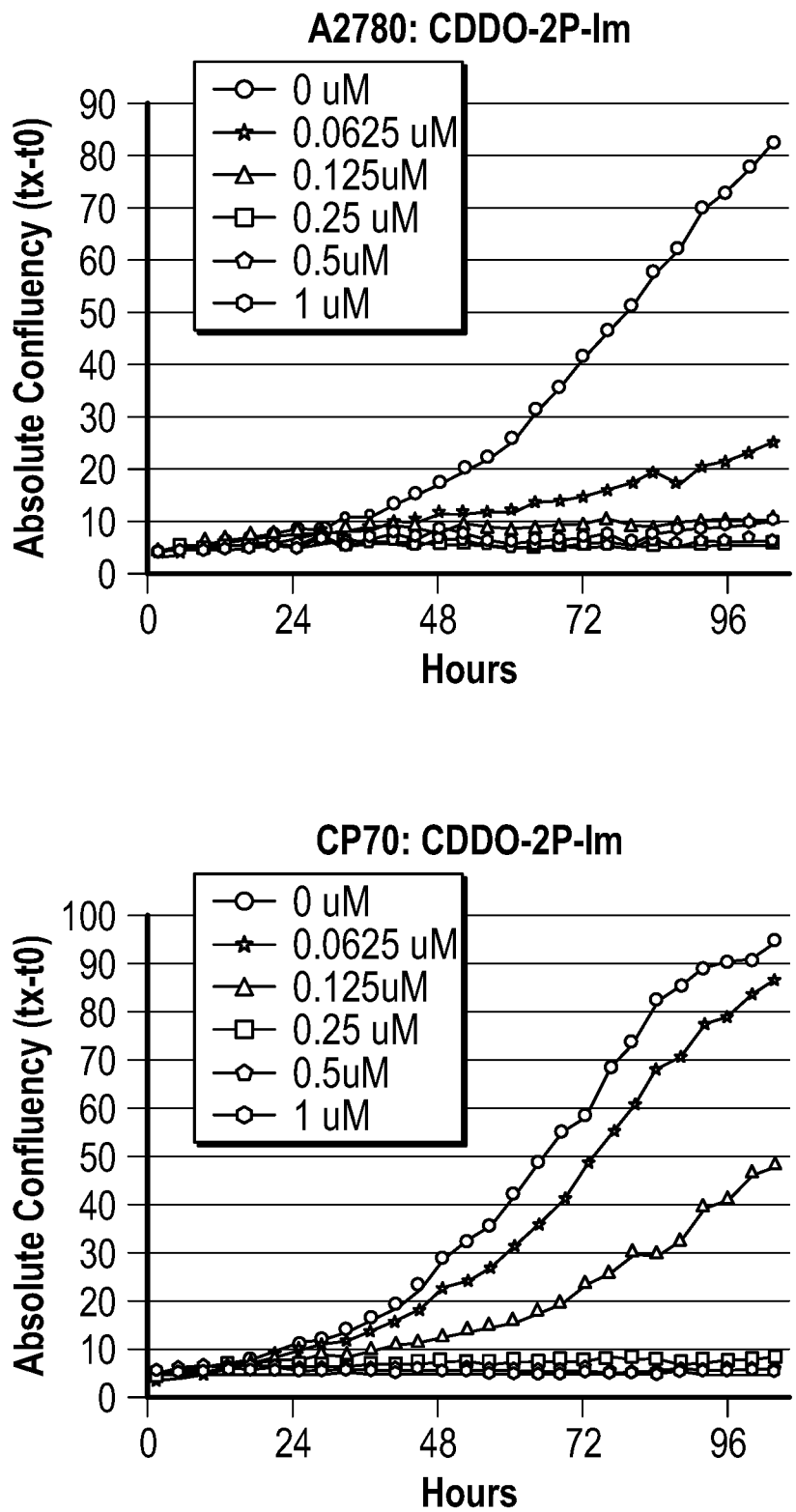
FIG. 11 is a set of line graphs. Cisplatin resistant human ovarian cancer cell lines A2780, CP70, OV81, CP10, OVCAR-5 and OVCAR-8 were exposed to CDDO-2P-Im, cisplatin, or a combination of CDDO-2P-Im and cisplatin. The data reveal that platinum-resistant cell lines are highly sensitive to CDDO-2P-Im. Moreover, a significant gain in ovarian cancer cell kill is observed when suboptimal doses of CDDO-2P-Im are combined with a cisplatin dose that alone has absolutely no effect in either A2780, CP70, OV81, CP10, OVCAR-5 and OVCAR-8 cells (significance at 0.005 or greater).
Figure 11:
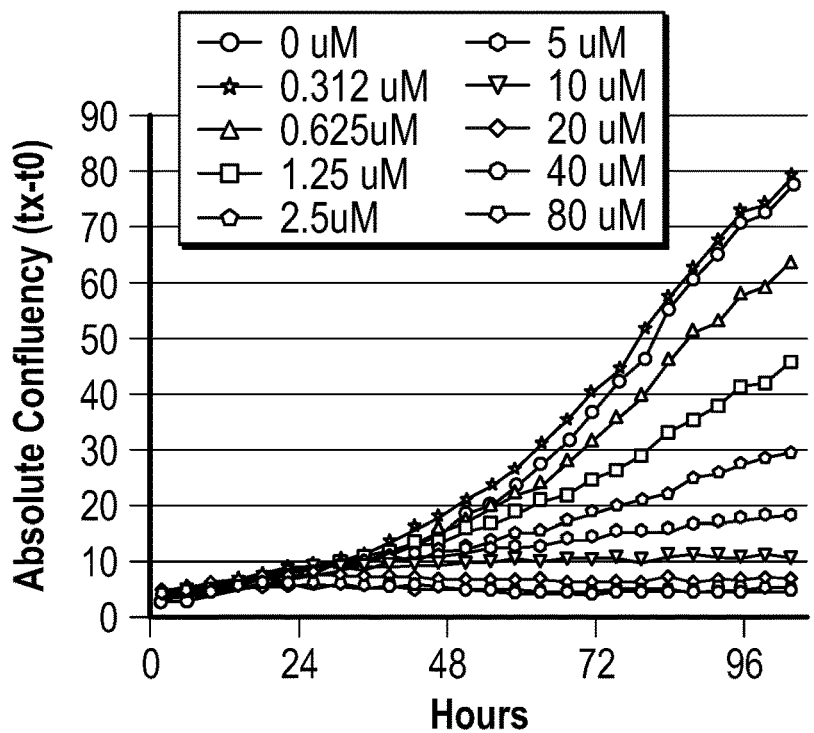
Figure 11:
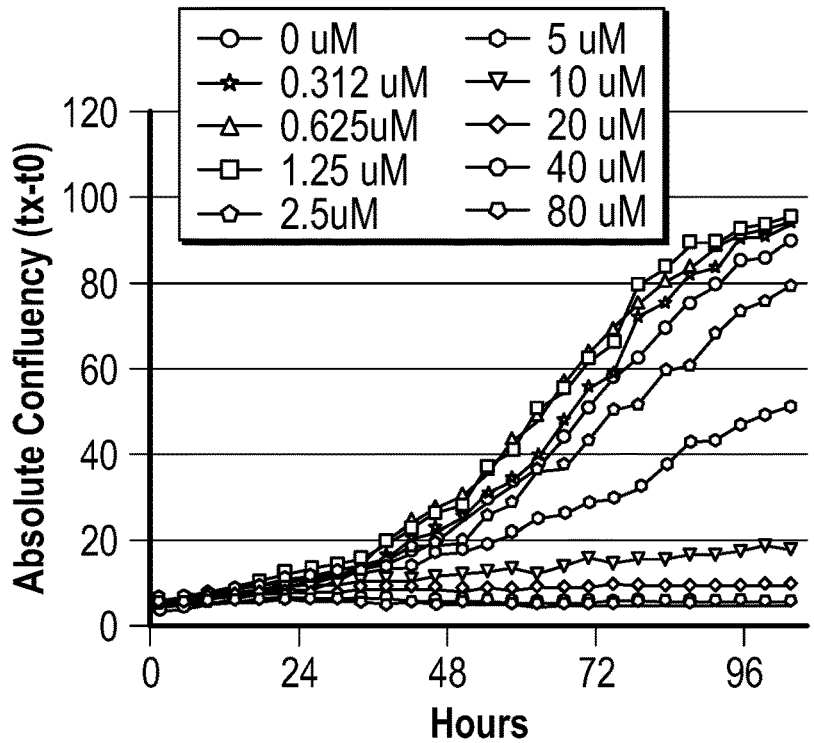
Figure 11:
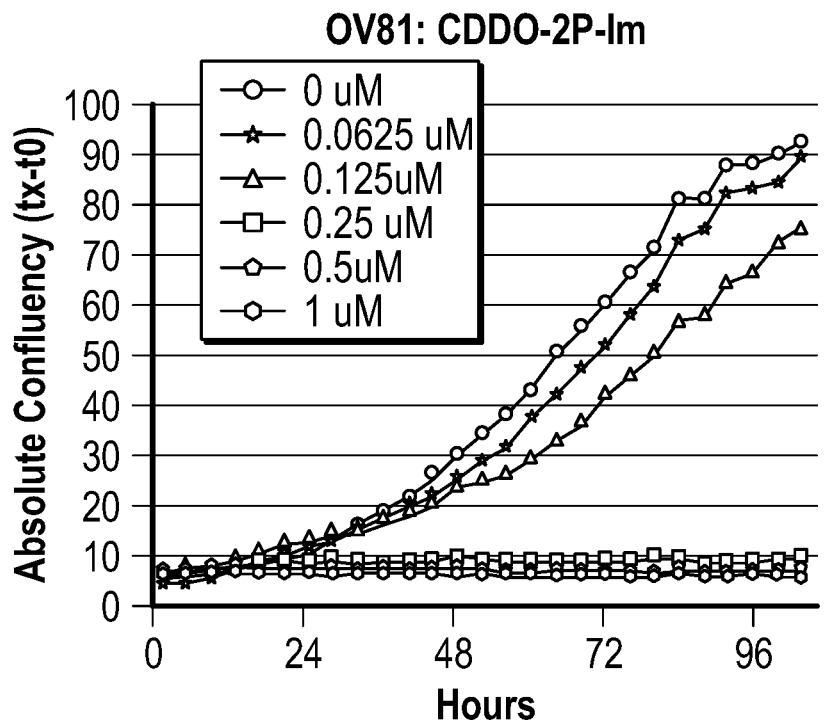
Figure 11:
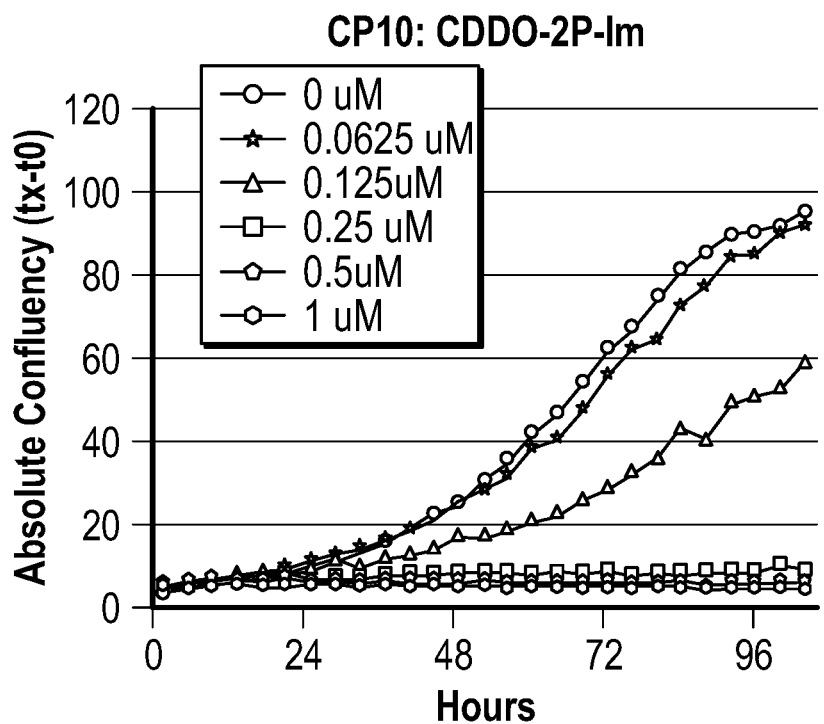
Figure 11:
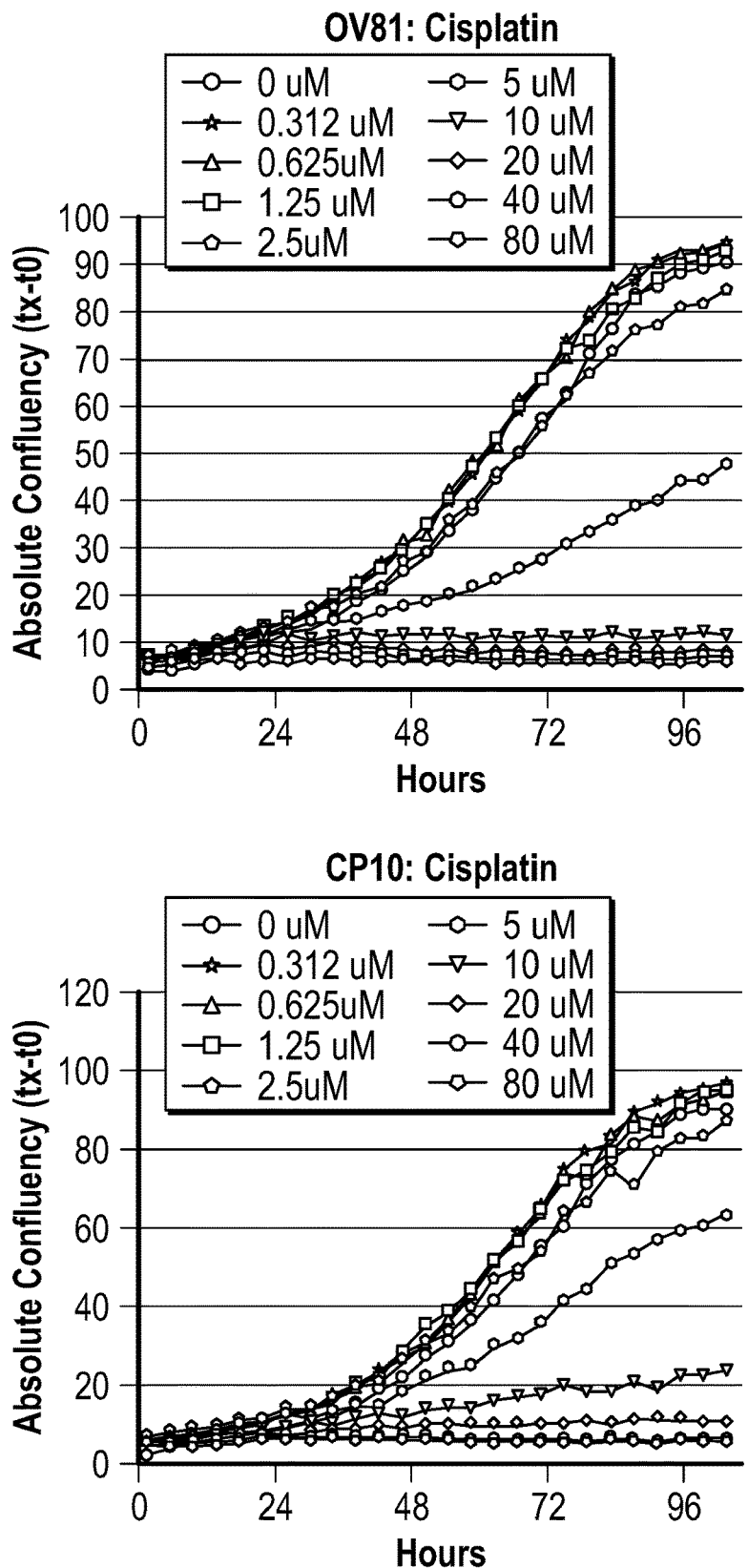
Figure 11:
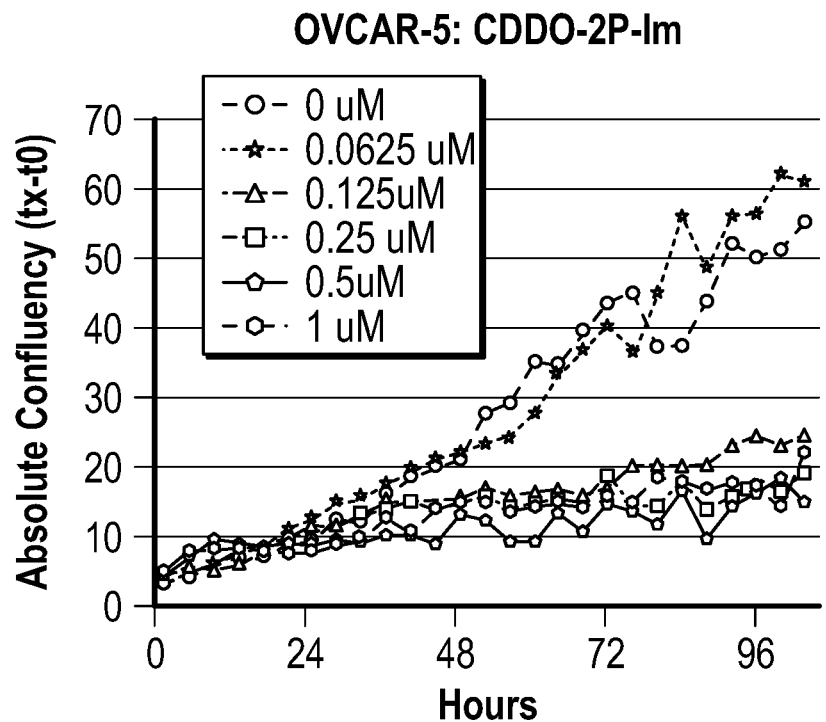
Figure 11:
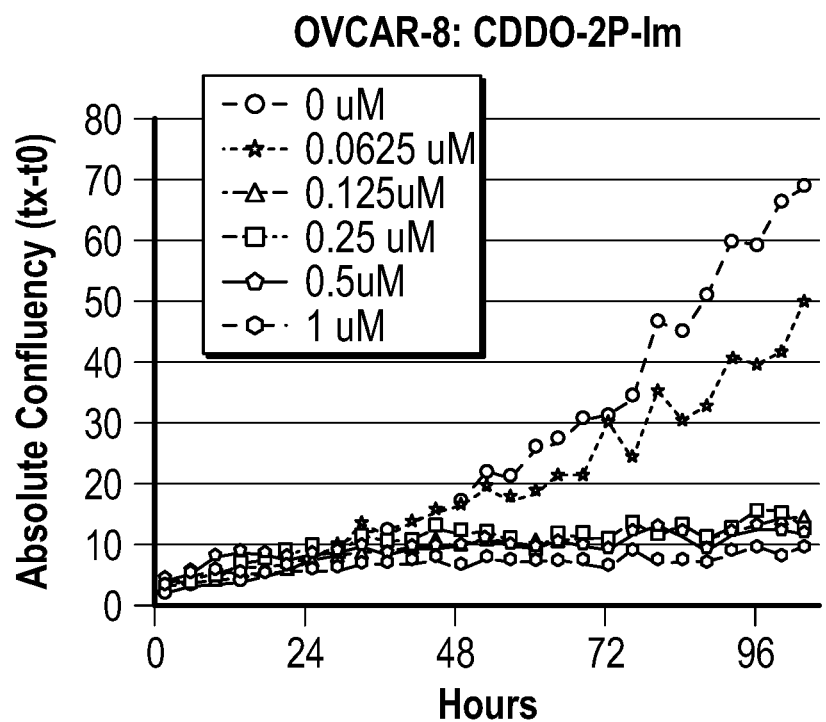
Figure 11:
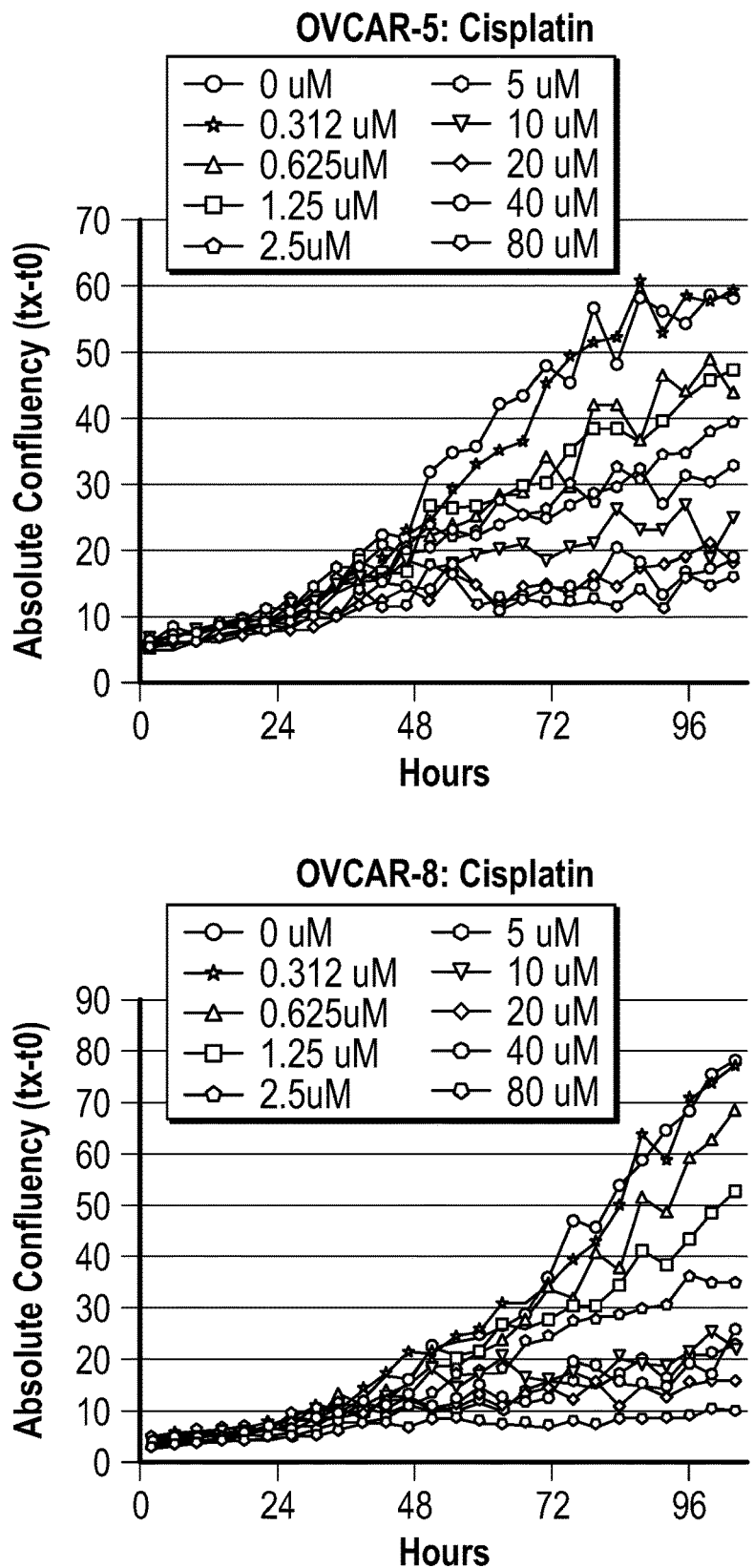
Figure 11:
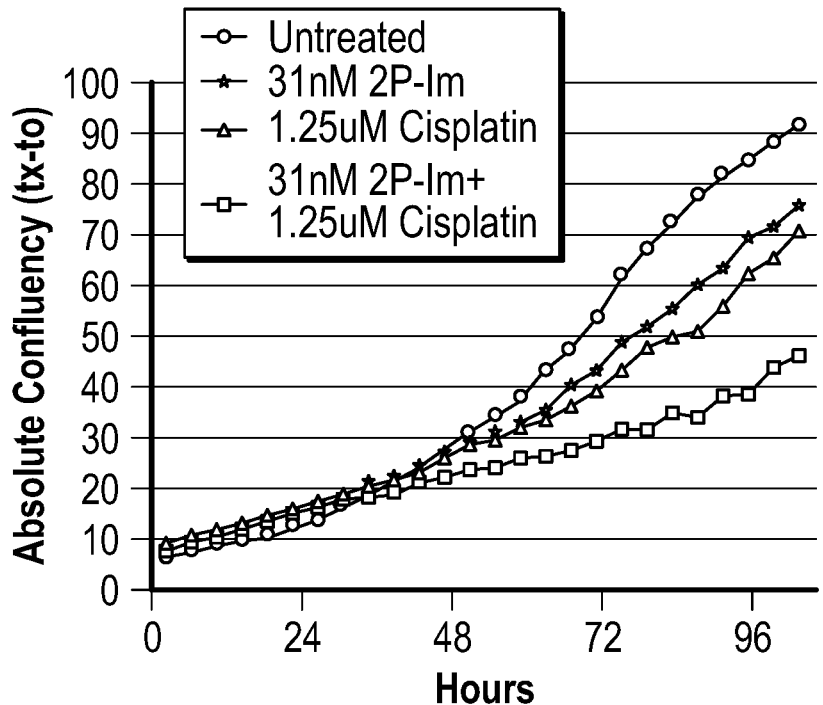
Figure 11:
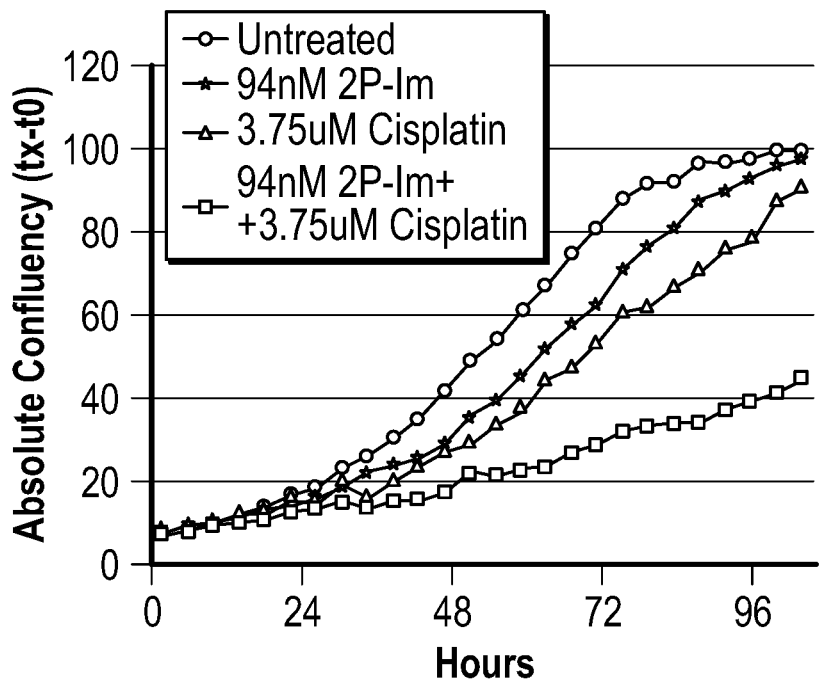
Figure 11:
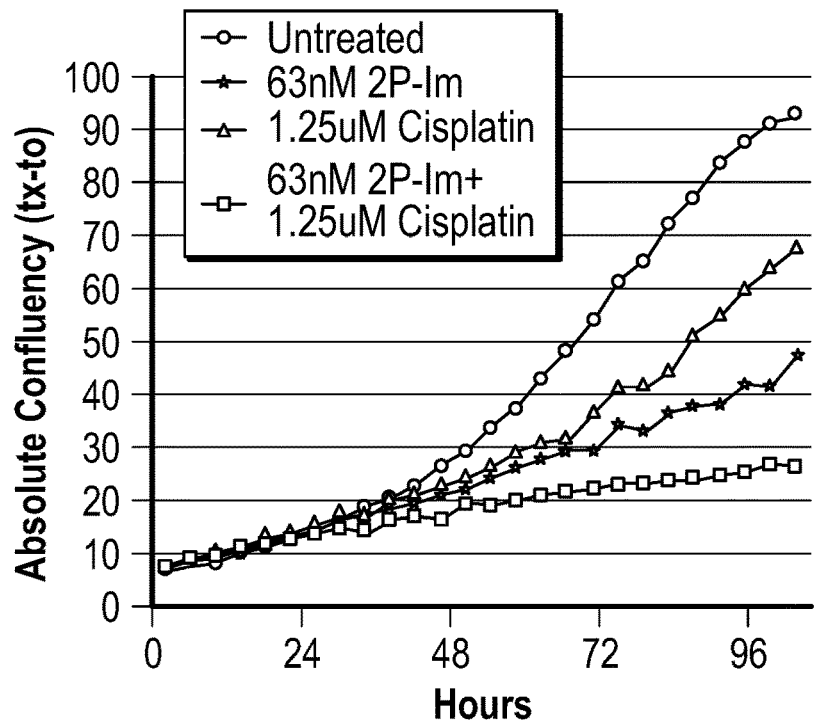
Figure 11:
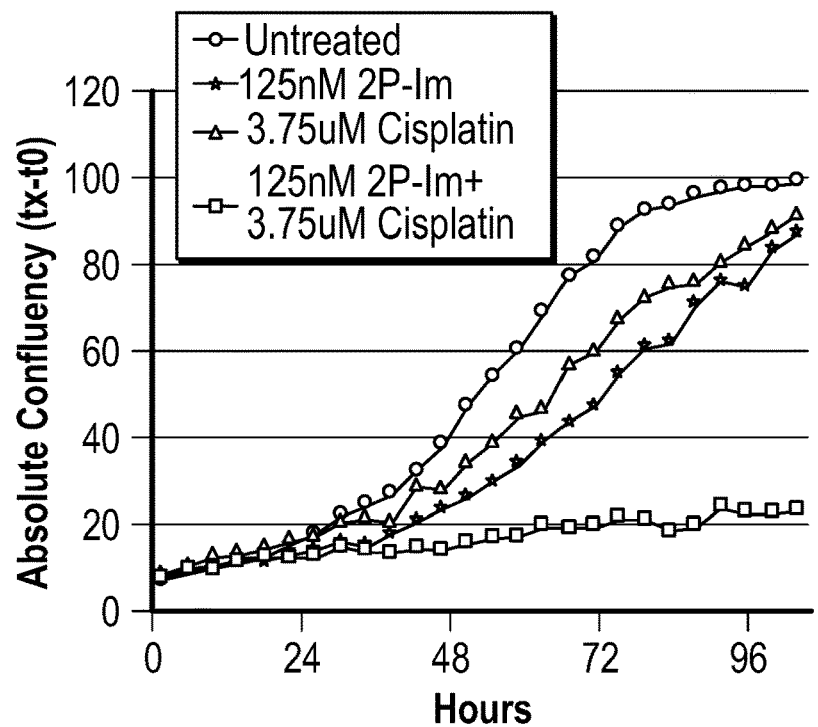
Figure 11:
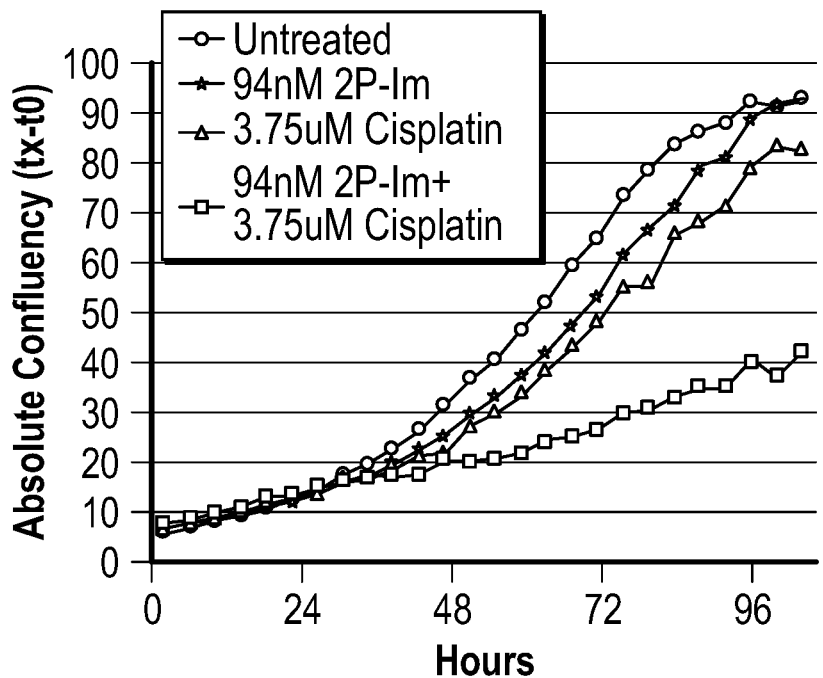
Figure 11:
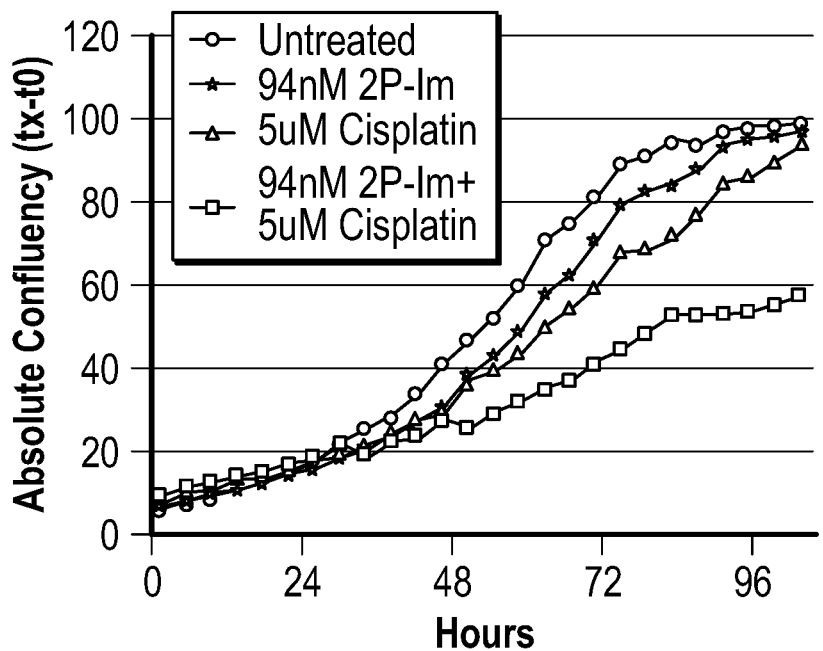
Figure 11:
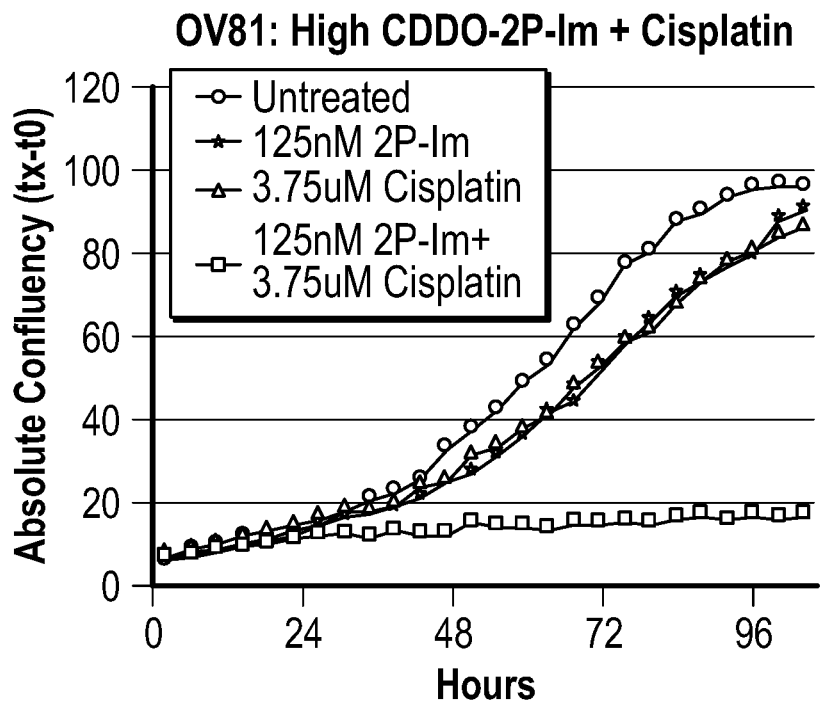
Figure 11:
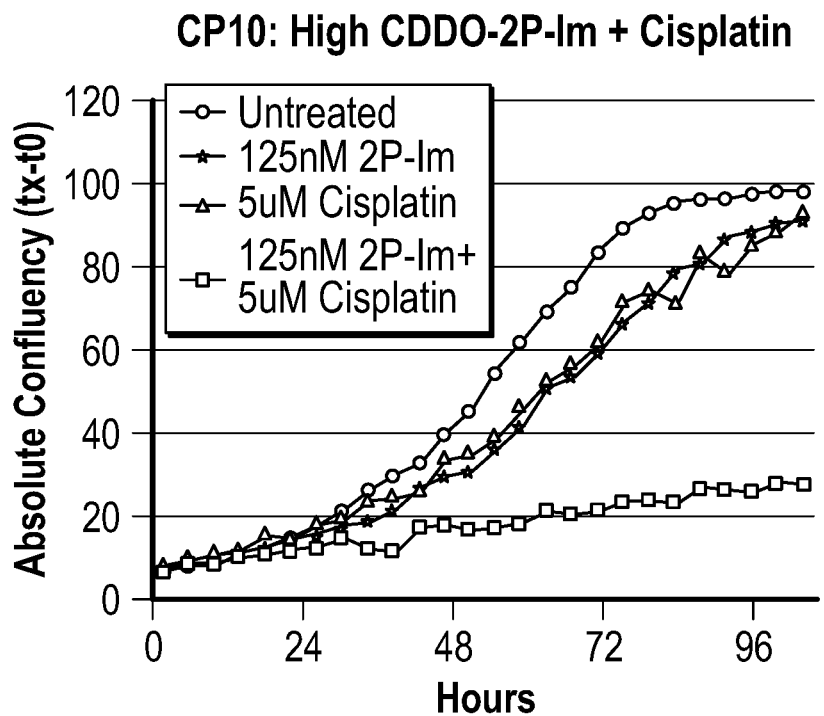
Figure 11:
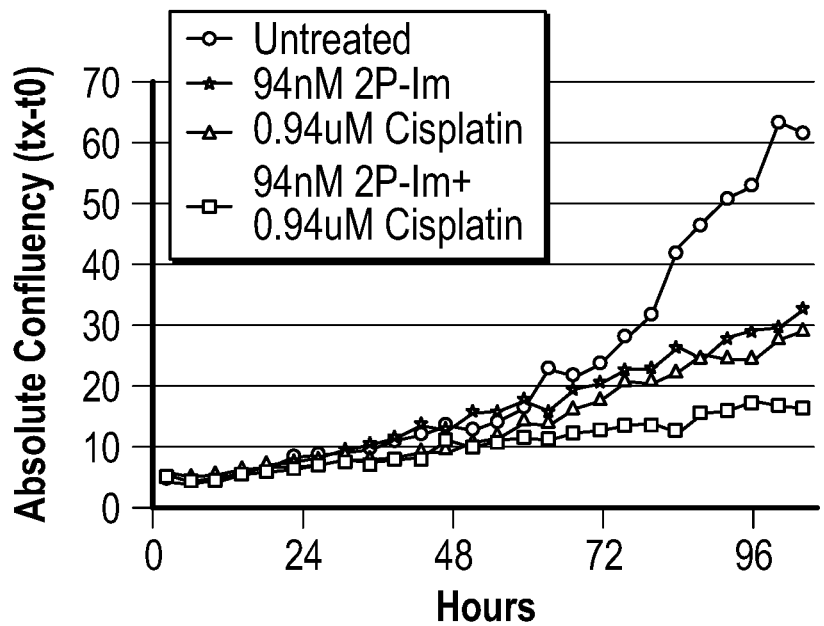
Figure 11:
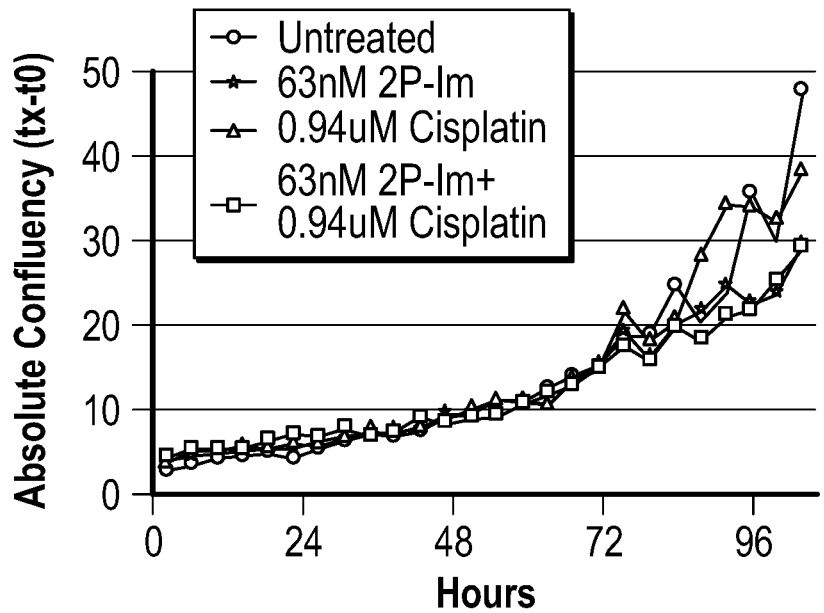
Figure 11:
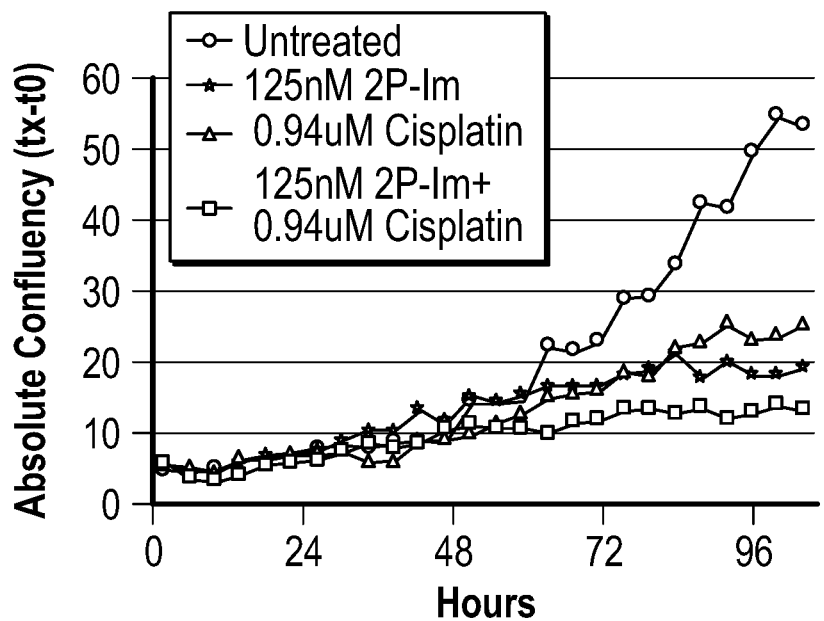
Figure 11:
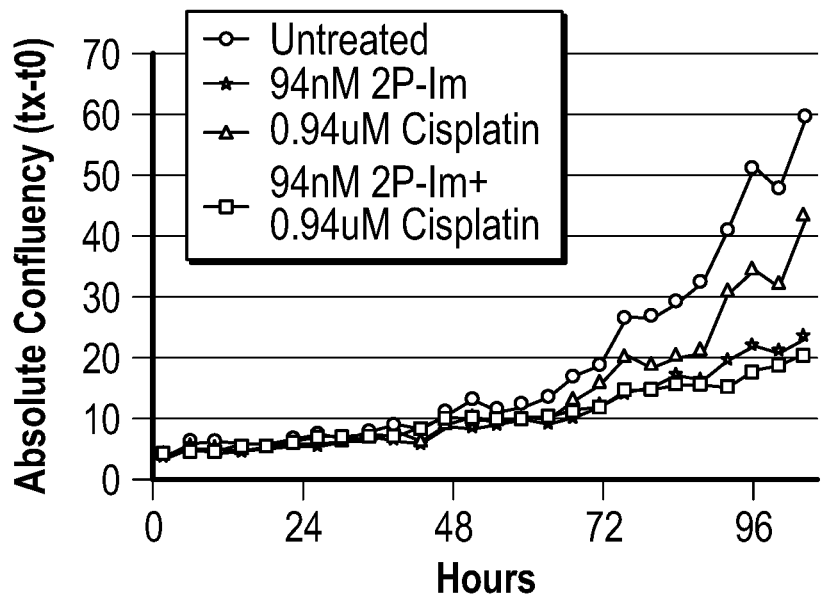

CDDO-2P-Im suppresses growth of cisplatin-resistant human ovarian cancer cells in vitro. Cisplatin resistant human ovarian cancer cell lines A2780, CP70, OV81, CP10, OVCAR-5 and OVCAR-8 cell were each cultured in a complete medium consisting of RPMI1640, 20% heat-inactivated FBS, 1% penicillin/streptomycin. Cells were cultured in a water jacketed $CO_2$ incubator at 37° C. in a humidified atmosphere consisting of 5% $CO_2$ and 95% air. Continuous live-cell analysis (CLCA) was used as a non-invasive cell monitoring and measurement method based on time-lapse, phase-contrast microscopy and fluorescence imaging, using IncuCyte® ZOOM. Cells were seeded in 96-well plates at densities of either $1\times10^4$ or $3\times10^4$ cell/cm$^2$ followed by addition of a drug dilution series for either CDDO-2P-Im or Cisplatin (P4394, Sigma) dissolved in PBS and diluted in media. Exposure of ovarian cancer cell lines A2780 (FIG. 11, left panels) and CP70 (FIG. 11, right panels) to CDDO-2P-Im suppressed growth in a dose-dependent manner at nanomolar (nM) concentrations, defined by confluence assessed in the Incucyte® system. Reduction in confluence is accompanied by the detachment and death of ovarian cancer cells. The data reveal that these platinum-resistant cell lines are highly sensitive to CDDO-2P-Im. Moreover, a significant gain in ovarian cancer cell kill is observed when suboptimal doses of CDDO-2P-Im are combined with a cisplatin dose that alone has absolutely no effect in either A2780, CP70, OV81, CP10, OVCAR-5 and OVCAR-8 cells (significance at 0.005 or greater).

CDDO-2P-Im synergistically inhibits proliferation of ovarian cancer cells in combination with cisplatin in vitro.

Data presented herein show that CDDO-2P-Im has activity against a number of human ovarian and endometrial cancer cell lines. Moreover, CDDO-2P-Im has the ability to kill variants with known resistance to cisplatin. Finally, CDDO-2P-Im acts synergistically with cisplatin to inhibit proliferation of such cancer cells in vitro.

These data support the potential for CDDO-2P-Im to augment standard chemotherapy regimens involving a platinum compound.

The invention claimed is:

1. A method for treating glioma in a patient identified as having glioma, the method comprising administering CDDO-2P-Im to the patient, wherein the CDDO-2P-Im is administered in an amount effective to inhibit NLRP3 inflammasome and/or LON protease activity in the patient.

2. The method of claim 1, wherein the glioma is high grade glioma.

3. The method of claim 1, wherein the glioma is astrocytoma.

4. The method of claim 1, wherein the glioma is glioblastoma multiforme.

5. The method of claim 1, wherein the method further comprises co-administering a chemotherapeutic agent to the patient.

6. The method of claim 5, wherein the chemotherapeutic agent is an alkylating agent.

7. The method of claim 6, wherein the alkylating agent is temozolomide (TMZ).

8. The method of claim 7, wherein the method reduces a side effect associated with TMZ, wherein the side effect associated with TMZ is lymphopenia.

9. The method of claim 1, wherein the patient further receives radiation therapy.

10. The method of claim 1, wherein the glioma is temozolomide-resistant glioma.

11. A method for treating a cancer in a patient identified as having the cancer, the method comprising administering CDDO-2P-Im to the patient, wherein the CDDO-2P-Im is administered in an amount effective to inhibit NLRP3 inflammasome and/or LON protease activity in the patient, wherein the cancer is glioma, multiple myeloma, or ovarian cancer.

12. The method of claim 11, wherein the cancer is multiple myeloma and the method further comprises co-administering a proteasome inhibitor to the patient.

13. The method of claim 12, wherein the method reduces a side effect associated with the proteasome inhibitor, wherein the side effect associated with the proteasome inhibitor is neuropathic pain.

14. The method of claim 12, wherein the proteasome inhibitor is bortezomib, carfilzomib, or ixazomib.

15. A method for treating glioma in a patient identified as having glioma, the method comprising administering an effective amount of CDDO-2P-Im to the patient.

16. The method of claim 15, further comprising administering temozolomide (TMZ) to the patient.

17. The method of claim 16, wherein the method reduces a side effect associated with TMZ, wherein the side effect associated with TMZ is lymphopenia.

18. The method of claim 15, wherein the glioma is high grade glioma.

19. The method of claim 15, wherein the glioma is glioblastoma multiforme.

* * * * *